US011953376B2

(12) United States Patent
Takashima

(10) Patent No.: US 11,953,376 B2
(45) Date of Patent: Apr. 9, 2024

(54) IMAGING APPARATUS, SIGNAL PROCESSING APPARATUS, SIGNAL PROCESSING METHOD, AND PROGRAM

(71) Applicant: Sony Group Corporation, Tokyo (JP)

(72) Inventor: Masatoshi Takashima, Tokyo (JP)

(73) Assignee: Sony Group Corporation, Tokyo (JP)

( * ) Notice: Subject to any disclaimer, the term of this patent is extended or adjusted under 35 U.S.C. 154(b) by 559 days.

(21) Appl. No.: 17/263,368

(22) PCT Filed: Jul. 23, 2019

(86) PCT No.: PCT/JP2019/028765
§ 371 (c)(1),
(2) Date: Jan. 26, 2021

(87) PCT Pub. No.: WO2020/026882
PCT Pub. Date: Feb. 6, 2020

(65) Prior Publication Data
US 2021/0144345 A1    May 13, 2021

(30) Foreign Application Priority Data

Aug. 2, 2018 (JP) ................................ 2018-146164

(51) Int. Cl.
*G01J 3/02* (2006.01)
*A61B 1/00* (2006.01)
(Continued)

(52) U.S. Cl.
CPC ...... *G01J 3/0205* (2013.01); *A61B 1/000095* (2022.02); *A61B 1/00042* (2022.02);
(Continued)

(58) Field of Classification Search
CPC .. B64U 2101/30; B64C 39/024; H04N 23/16; H04N 9/03; H04N 25/11;
(Continued)

(56) References Cited

U.S. PATENT DOCUMENTS 9,173,554 B2 * 11/2015 Fengler .................... H04N 5/33
11,137,271 B2 * 10/2021 Seeley ............... G01M 11/3172
(Continued)

FOREIGN PATENT DOCUMENTS

EP          2284509 A1    2/2011
JP       2008518229 A    5/2008
(Continued)

OTHER PUBLICATIONS

International Search Report (PCT/ISA/210), International Application No. PCT/JP2019/028765, dated Oct. 9, 2019.
(Continued)

*Primary Examiner* — Marly S Camargo
(74) *Attorney, Agent, or Firm* — Michael Best & Friedrich LLP

(57) ABSTRACT

Provided is an imaging apparatus including: a splitter that splits incident light into pieces of light of two or more wavelength bands; and two or more detectors that detect the pieces of light of two or more wavelength bands respectively and output signals from which wavelengths can be extracted tunably by post-processing.

18 Claims, 23 Drawing Sheets

(51) Int. Cl.
- *B64C 39/02* (2023.01)
- *B64U 101/30* (2023.01)
- *G02B 27/14* (2006.01)
- *H04N 9/03* (2023.01)
- *H04N 23/16* (2023.01)
- *H04N 25/11* (2023.01)

(52) U.S. Cl.
CPC ........ *A61B 1/00163* (2013.01); *G02B 27/141* (2013.01); *H04N 9/03* (2023.01); *H04N 25/11* (2023.01); *B64C 39/024* (2013.01); *B64U 2101/30* (2023.01)

(58) Field of Classification Search
CPC ....... G01J 2003/1213; G01J 2003/2826; G01J 3/0205; A61B 1/00163; A61B 1/00009; A61B 1/00042; G02B 27/141
See application file for complete search history.

(56) References Cited

U.S. PATENT DOCUMENTS

| | | | |
|---|---|---|---|
| 11,298,022 B2* | 4/2022 | Fengler | G01J 3/0205 |
| 2008/0123097 A1 | 5/2008 | Muhammed et al. | |
| 2012/0193520 A1* | 8/2012 | Bewrsdorf | G02B 27/141 |
| | | | 250/226 |
| 2018/0128600 A1* | 5/2018 | 'THooft | A61B 1/00163 |

FOREIGN PATENT DOCUMENTS

| | | |
|---|---|---|
| JP | 2008136251 A | 6/2008 |
| JP | 2011528918 A | 12/2011 |
| JP | 2013108788 A | 6/2013 |
| WO | 2009/117483 A1 | 9/2009 |
| WO | WO-2016208415 A1 | 12/2016 |

OTHER PUBLICATIONS

International Written Opinion (PCT/ISA/237), International Application No. PCT/JP2019/028765, dated Oct. 9, 2019.

Geelen Bert et al. "System-level analysis and design for RGB-NIR CMOS camera", Proceedings of SPIE; [Proceedings of SPIE ISSN 0277-786X vol. 10524], SPIE, US, vol. 10110, Feb. 20, 2017 (Feb. 20, 2017), pp. 101100B-101100B, XP060083370, DOI: 10 .1117 /12. 2250852 ISBN: 978-1-5106-1533-5 the whole document.

* cited by examiner

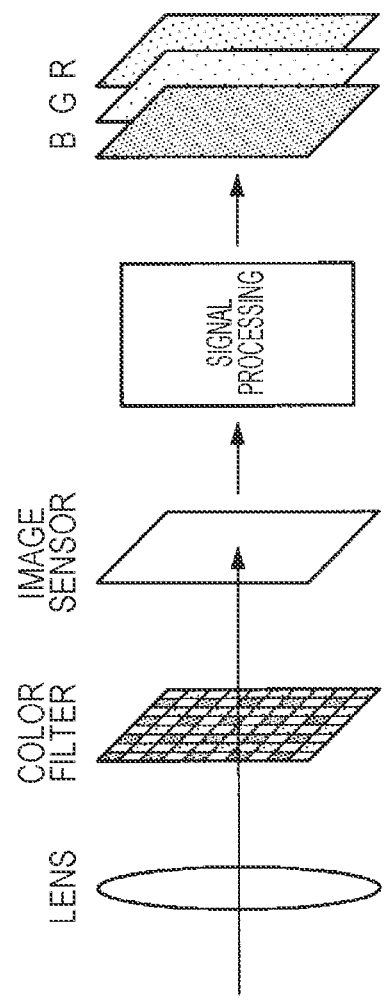
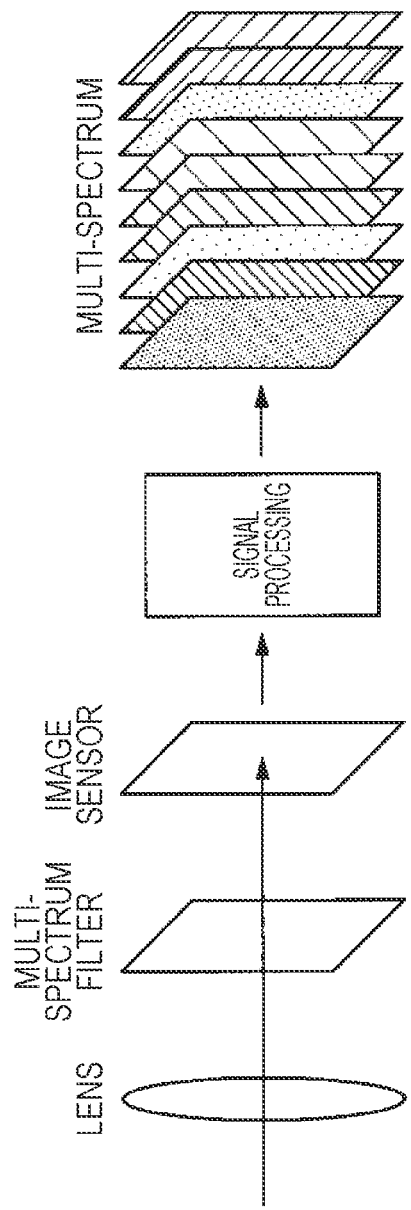
FIG. 1A
FIG. 1B

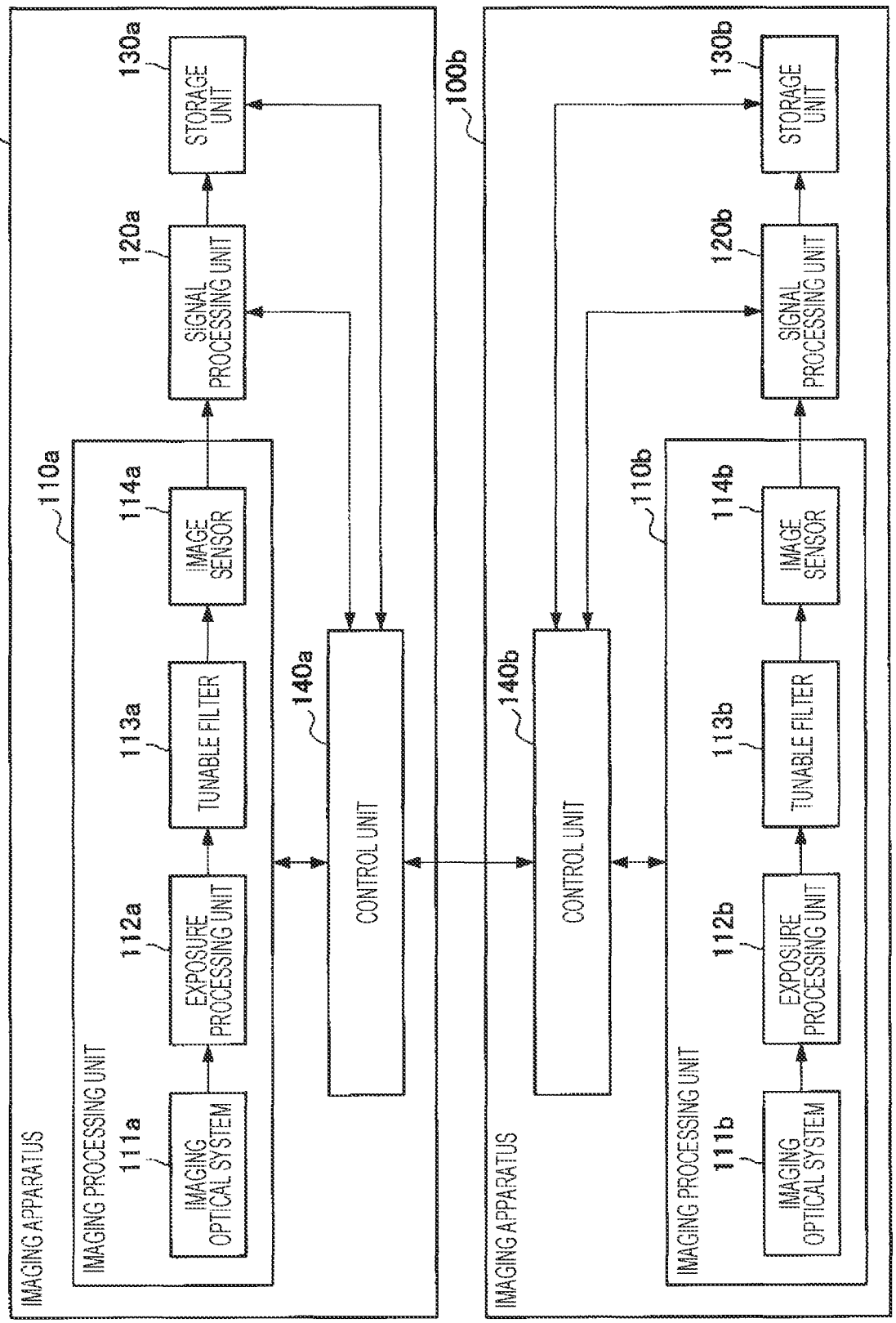

IMAGING APPARATUS, SIGNAL PROCESSING APPARATUS, SIGNAL PROCESSING METHOD, AND PROGRAM

CROSS REFERENCE TO RELATED APPLICATIONS

This application claims the benefit of Japanese Priority Patent Application JP 2018-146164 filed on Aug. 2, 2018, the entire contents of which are incorporated herein by reference.

TECHNICAL FIELD

The present disclosure relates to an imaging apparatus, a signal processing apparatus, a signal processing method, and a program.

BACKGROUND ART

In recent years, an apparatus or a system capable of acquiring multiband images having a larger number of multiple bands more than the three RGB bands has been developed. For example, PTL 1 discloses a multi-spectrum camera capable of acquiring multiband images with resolution and sensitivity substantially comparable to those of RGB three-band cameras in related art.

CITATION LIST

Patent Literature

[PTL 1]
JP 2008-136251A

SUMMARY

Technical Problem

However, when an image of a desired wavelength band is extracted using a multi-spectrum camera including that disclosed in PTL 1 (hereinafter, a feature of being capable of extracting an image of a desired wavelength band will be referred to as "being tunable"), there are cases in which it is difficult to maintain high wavelength reproducibility and a high S/N ratio. More specifically, when a wide wavelength band ranging from a visible band to a band (for example, a near-infrared (NIR) band) other than the visible band is to be covered by one multi-spectrum filter, the reproducibility of an extraction target wavelength may deteriorate remarkably. Moreover, when signal components of wavelengths other than the extraction target wavelength are large, for example, the signal components of the extraction target wavelength may decrease.

Therefore, the present disclosure has been made in view of the above-described problems, and it is desirable to provide an imaging apparatus, a signal processing apparatus, a signal processing method, and a program which are novel or improved and can extract a wavelength tunably while maintaining high wavelength reproducibility and a high S/N ratio.

Solution to Problem

According to the present disclosure, an imaging apparatus including a splitter that splits incident light into pieces of light of two or more wavelength bands; and two or more detectors that detect the pieces of light of two or more wavelength bands respectively and output signals from which wavelengths can be extracted tunably by post-processing is provided.

Moreover, according to the present disclosure, a signal processing apparatus including an acquiring unit that acquires signals output by two or more detectors respectively having detected pieces of light of two or more wavelength bands split from incident light by a splitter; and a signal processing unit that extracts signals of a desired wavelength band using the signals is provided.

Moreover, according to the present disclosure, a signal processing method to be executed by a computer, the method including acquiring signals output by two or more detectors respectively having detected pieces of light of two or more wavelength bands split from incident light by a splitter; and extracting signals of a desired wavelength band using the signals is provided.

Moreover, according to the present disclosure, a program for causing a computer to execute: acquiring signals output by two or more detectors respectively having detected pieces of light of two or more wavelength bands split from incident light by a splitter; and extracting signals of a desired wavelength band using the signals is provided.

Advantageous Effects of Invention

As described above, according to the present disclosure, it is possible to extract a wavelength tunably while maintaining high wavelength reproducibility and a high S/N ratio.

Here, the above-described effects are not necessarily limitative. With or in the place of the effects, any one of the effects described in this specification or other effects that may be grasped from this specification may be provided.

BRIEF DESCRIPTION OF DRAWINGS

FIGS. 1A and 1B are diagrams illustrating a difference between an RGB camera in related art and a multi-spectrum camera.

FIG. 13 is a block diagram illustrating a configuration example of an imaging apparatus 100a and an imaging apparatus 100b according to the second embodiment.

DESCRIPTION OF EMBODIMENTS

Figure 2A:
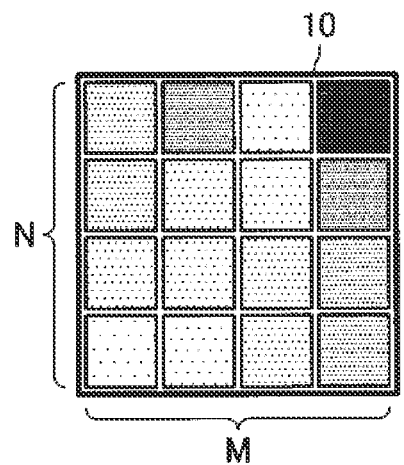
FIGS. 2A and 2B are diagrams illustrating a tunable filter 113 included in an imaging apparatus 100.

Hereinafter, preferred embodiments of the present disclosure will be described in detail with reference to the appended drawings. Here, in this specification and the appended drawings, configurative elements that have substantially the same function and configuration are denoted with the same reference numerals, and repeated explanation of these configurative elements is omitted.

Here, description will be given in the following order.
1. Background
2. First Embodiment
2.1. Overview
2.2. Configuration Example
2.3. Example of Flow of Signal Processing
3. Second Embodiment
4. Application Example
4.1. Application Example to Medical Imaging Apparatus
4.2. Application Example to Operating Room System
4.3. Application Example to Vehicle Control System

1. BACKGROUND

In recent years, an apparatus or a system capable of acquiring multiband images having a larger number of multiple bands more than the three RGB bands has been developed. For example, PTL 1 discloses a multi-spectrum camera capable of acquiring multiband images with resolution and sensitivity substantially comparable to those of RGB three-band cameras in related art.

Here, a difference between an RGB camera in related art and a multi-spectrum camera will be described with reference to FIGS. 1A and 1B. FIG. 1A illustrates an overview of a configuration of an RGB camera in related art, in which light is incident on the RGB camera in the order of a lens, a color filter (for example, a color filter of the Bayer arrangement), and an image sensor and an RGB image is acquired by subsequent signal processing (or developing processing).

FIG. 1B illustrates an overview of a configuration of a multi-spectrum camera, and the multi-spectrum camera includes a multi-spectrum filter instead of the color filter included in the RGB camera. Due to this, incident light is separated in a larger number of wavelength bands than the RGB bands and a multi-spectrum image is acquired by subsequent image processing.

There are roughly two method of acquiring multi-spectrum images. A first method is a method of acquiring multi-spectrum images by collecting pixel data generated by incident light passing via multi-spectrum filters when the respective multi-spectrum filters have spectral characteristics of transmitting narrow-band light. For example, an image sensor in which resonance paths having different heights for respective pixels are formed in an upper part of the image sensor whereby multi-spectrum filters having narrow-band (half-value width of approximately 10 to 20 [nm]) spectral characteristics are formed has already been developed. For example, an image sensor of 2048×1088 pixels in which 16 types of narrow-band multi-spectrum filters are formed in units of 4×4 pixels has been developed. In the image sensor, demosaic processing (collection of respective pixels, intra-space filtering processing, and the like) is performed on raw data acquired from the image sensor whereby multi-spectrum images are acquired. Here, the half-width value used in the present disclosure means the width between wavelengths having a filter transmittance of approximately 50 [%] (however, there is no limitation thereto).

The other method is a method of acquiring images of a desired wavelength band by performing an inverse matrix operation with respect to pixels having passed through multi-spectrum filters when the respective multi-spectrum filters have spectral characteristics of transmitting wide-band light. For example, a technology in which 32×32 (1024) types of different filters are formed in an image sensor, and demosaic processing is performed on raw data acquired from the image sensor and an inverse matrix operation is performed thereon subsequently whereby images of a super-narrow band (half-width value of several nanometers [nm]) are acquired has been developed. In this technology, a multi-spectrum filter which uses plasmon resonance stimulated by incident light can be used.

Here, as described above, when a tunable wavelength is extracted using a multi-spectrum camera in related art including that disclosed in PTL 1, there are cases when it is difficult to maintain high wavelength reproducibility and a high S/N ratio. More specifically, when a wide wavelength band ranging from a visible band to a band (for example, a near-infrared band) other than the visible band is to be covered by one multi-spectrum filter, the reproducibility of an extraction target wavelength may deteriorate remarkably. Moreover, when signal components of wavelengths other than the extraction target wavelength are large, for example, the signal components of the extraction target wavelength may decrease.

For example, a case in which vegetation (plant) is a subject and a vegetation index is calculated on the basis of spectral characteristics when vegetation reflects sunlight will be discussed. The reflectance of vegetation differs greatly from visible band to near-infrared band. Due to this, when reflection light reflected by vegetation is covered by one multi-spectrum filter, since the percentage of signal components of the near-infrared band in the entire signal components increases, the wavelength reproducibility and S/N ratio of the signal components of the visible band are impaired greatly.

Therefore, the discloser of the present disclosure has reached to invent the technology of the present disclosure in view of the above-described problems. An imaging apparatus 100 according to an embodiment of the present disclosure includes a splitter that splits incident light into pieces of light of two or more wavelength bands and two or more detectors that detect the pieces of light of two or more wavelength bands and output signals from which wavelengths can be extracted tunably by post-processing. In this way, for example, the imaging apparatus 100 can extract wavelengths tunably while maintaining high wavelength reproducibility and a high S/N ratio by splitting incident light into light of a visible band and light of a near-infrared band and covering the respective light beams using two multi-spectrum filters. Hereinafter, the present disclosure will be described in detail.

2. FIRST EMBODIMENT

2.1. Overview

First, an overview of a first embodiment of the present disclosure will be described. Hereinafter, a case in which vegetation (plant) is a subject, spectral characteristics when vegetation reflects sunlight, and a vegetation index is output on the basis of the spectral characteristics will be described as an example. Here, this is an example only, and a target to which the present disclosure is applied is not particularly limited.

The imaging apparatus 100 according to the present embodiment includes a filter (hereinafter sometimes referred to as a "tunable filter 113" for the sake of convenience) disposed on a front stage of an image sensor 114 so as to transmit light of a wavelength band in which wavelengths can be extracted tunably. The tunable filter 113 has spectral characteristics of transmitting light of a wide band and the sensing sensitivity thereof tends to increase when combined with the image sensor 114 on a rear stage.

Figure 2B:
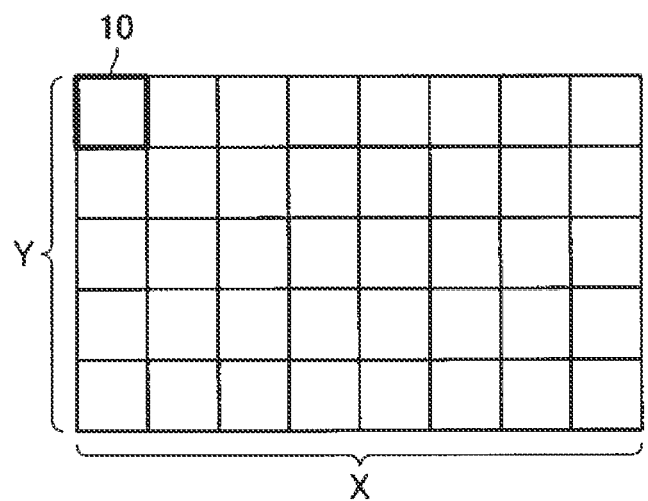

Here, the tunable filter 113 included in the imaging apparatus 100 will be described with reference to FIGS. 2A and 2B. FIGS. 2A and 2B are diagrams illustrating an example of the tunable filter 113. As illustrated in FIG. 2A, filters having different spectral characteristics in respective pixels 10 arranged in an M×N (in this drawing, 4×4) array form are disposed periodically in the imaging apparatus 100.

Moreover, as illustrated in FIG. 2B, the M×N pixels 10 are arranged in an X×Y array form whereby one tunable filter 113 is formed. Therefore, the imaging apparatus 100 can image M×X pixels in a horizontal direction and N×Y pixels in a vertical direction. Here, the tunable filter 113 included in the imaging apparatus 100 is not limited to the example of FIGS. 2A and 2B. For example, in FIG. 2A, the number of types of filters that form the tunable filter 113 is not particularly limited. Moreover, a periodic arrangement of filters may be changed appropriately and the filters may not be arranged periodically.

Figure 3:
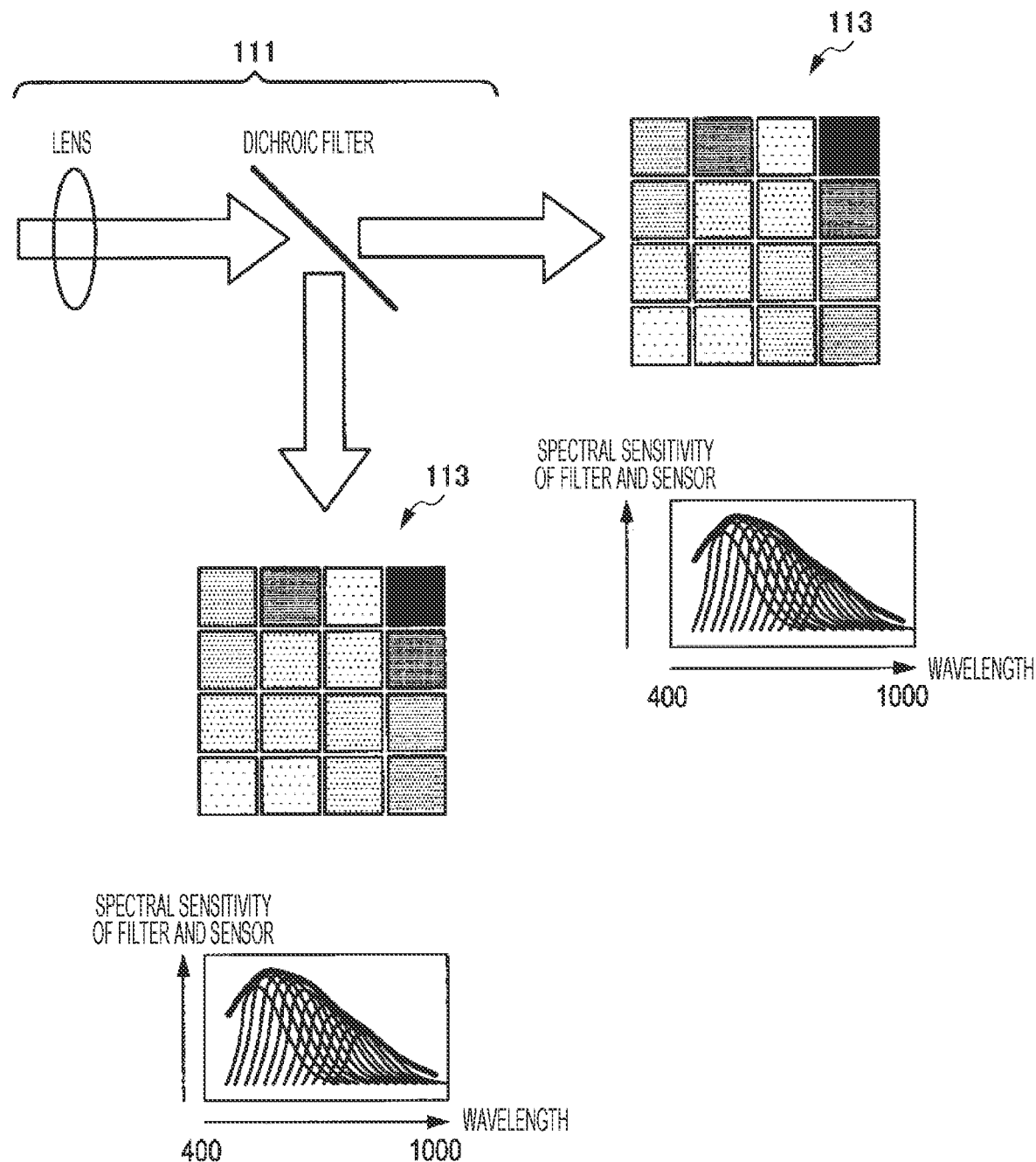
FIG. 3 is a diagram illustrating how incident light is split by the imaging apparatus 100 and the split light is detected.
Figure 4:
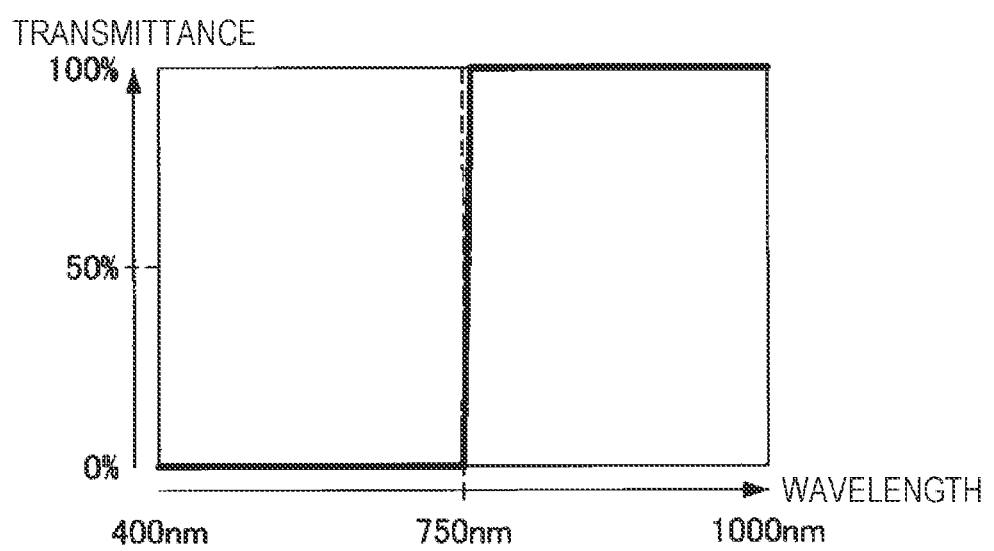
FIG. 4 is a diagram illustrating spectral characteristics of a dichroic filter.

The imaging apparatus 100 includes a number of tunable filters 113 (and image sensors 114) corresponding to the number of splits of incident light split into pieces of light of two or more wavelength bands by the splitter. For example, as illustrated in FIG. 3, the imaging apparatus 100 includes an imaging optical system 111 including a lens that receives incident light and a dichroic filter functioning as a splitter that splits the incident light into pieces of light of two wavelength bands. FIG. 4 illustrates an example of spectral characteristics of the dichroic filter. As illustrated in FIG. 4, the dichroic filter splits incident light into pieces of light of two wavelength bands by transmitting substantially 100 [%] of light of wavelengths longer than approximately 750 [nm] without transmitting light of wavelengths of approximately 750 [nm] or smaller. That is, the dichroic filter has a function of splitting incident light into light of a wavelength of the visible light (approximately 750 [nm] or smaller) and light of a wavelength longer than the wavelength of visible light. Here, the wavelength of a splitting point is not limited to 750 [nm] as long as it is possible to split incident light roughly into visible light and light on the longer wavelength side.

Moreover, the light beams split by the dichroic filter pass through the tunable filters 113 having approximately the same spectral characteristics and are detected by the image sensors 114. In this way, for example, when spectral characteristics of vegetation of which the reflectance differs greatly from visible band to near-infrared band are calculated, the imaging apparatus 100 can maintain a high S/N ratio and high wavelength reproducibility by preventing signal components of the visible band from being embedded in the signal components of the near-infrared band.

Figure 5:
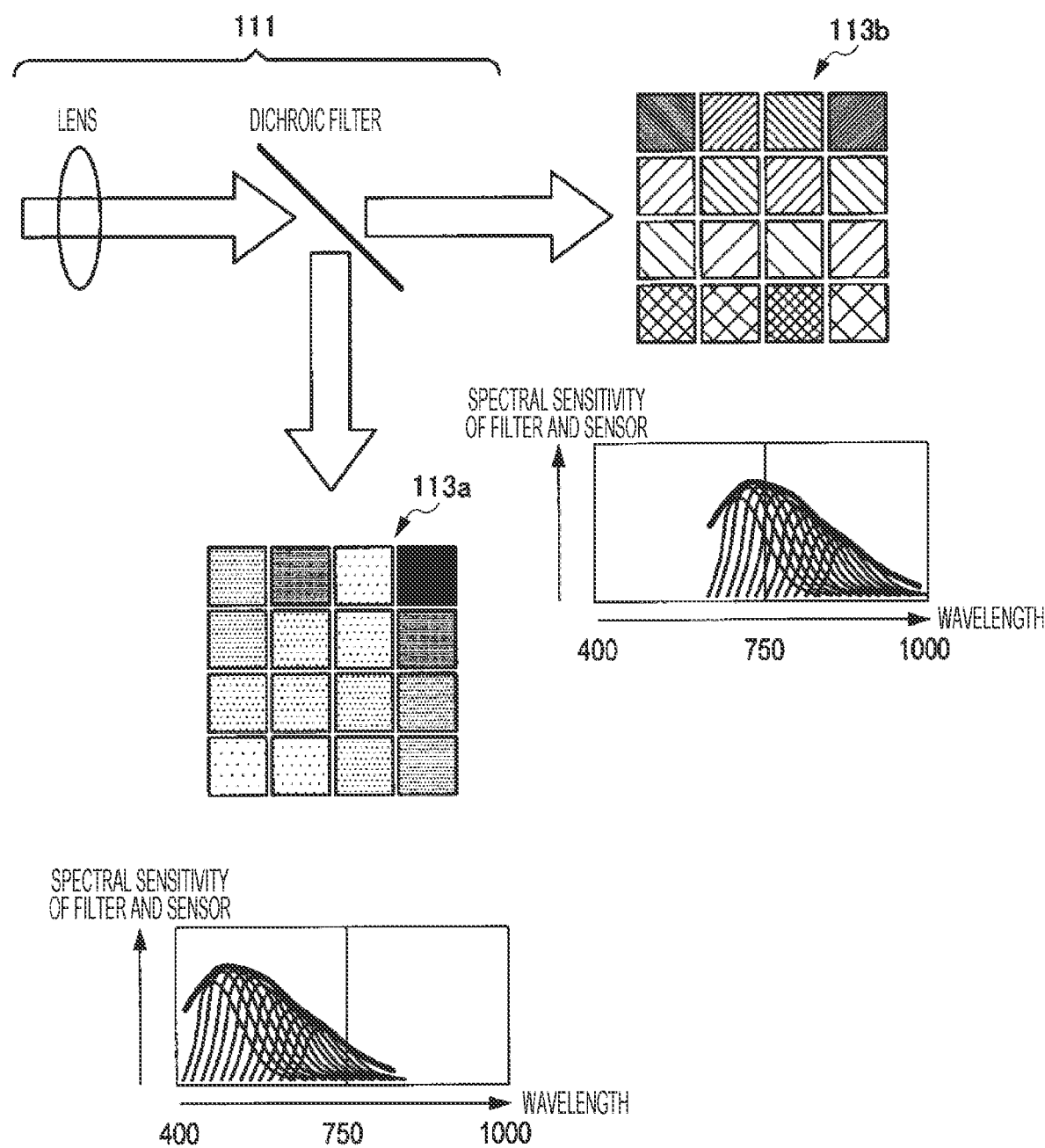
FIG. 5 is a diagram illustrating how incident light is split by the imaging apparatus 100 and the split light is detected.

Moreover, the imaging apparatus 100 may include tunable filters 113 having different spectral characteristics (here, the transmitting characteristics of the dichroic filter are similar to those illustrated in FIG. 4). For example, as illustrated in FIG. 5, the imaging apparatus 100 may use a tunable filter having stronger spectral sensitivity with respect to a wavelength band of approximately 750 [nm] or smaller as the tunable filter 113a on which light (light of a wavelength of approximately 750 [nm] or smaller) reflected by the dichroic filter is incident and may use a tunable filter having stronger spectral sensitivity with respect to a wavelength band longer than approximately 750 [nm] as the tunable filter 113b on which light (light of a wavelength longer than approximately 750 [nm]) having passed through the dichroic filter is incident. That is, the spectral characteristic of each of two or more detectors (the tunable filter 113 and the image sensor 114) may be determined depending on a wavelength band of detection target light. In this way, the imaging apparatus 100 can improve the S/N ratio and the wavelength reproducibility as compared to those of the configuration illustrated in FIG. 3.

Here, as illustrated in FIGS. 3 and 5, the imaging apparatus 100 splits an optical path of incident light into two or more optical paths using the dichroic filter that functions as a splitter. More specifically, the imaging apparatus 100 splits an optical path of incident light into two or more optical paths by including a dichroic filter in which a splitting surface is disposed so as to have a predetermined angle (for example, approximately 45°) with respect to an optical axis of the incident light. Here, the "optical axis of incident light" is a ray of light that represents the flux of incident light and is a ray of light that passes through the center of the flux of light. Moreover, the "splitting surface" is a surface that splits incident light into pieces of light of two or more wavelength bands, whereby the incident light is split into light reflected from the splitting surface and light passing through the splitting surface. Moreover, as illustrated in FIGS. 3 and 5, the imaging apparatus 100 has a number of tunable filters 113 (and image sensors 114) corresponding to the number of splits (the number of optical paths after splitting), disposed on the rear stage of the dichroic filter.

Here, the form of the imaging optical system 111, the tunable filter 113, and the like included in the imaging apparatus 100 is not limited to that described in FIGS. 3 and 5. For example, incident light may be split into three or more light beams. Moreover, an arbitrary optical system other than the dichroic filter may be used as the splitter. Moreover, the spectral characteristics of the dichroic filter and the tunable filter 113 are not particularly limited.

When the overview of the present embodiment is described from another viewpoint, the imaging apparatus 100 according to the present embodiment is mounted on an unmanned aerial vehicle (UAV) 20 including a drone and the like to image the ground from the air. Moreover, the image data acquired by the imaging apparatus 100 is used for calculating a predetermined vegetation index indicating the vegetation state and the spectral characteristics of vegetation on the ground.

In this case, the type of a vegetation index to be analyzed differs depending on the type of plant and a growth stage. For example, in a growth stage of dark green plant, analysis of a vegetation index called normalized difference vegetation index (NDVI) is effectively used for understanding the change in plant accurately. When NDVI is calculated, it is necessary to acquire image data of a wavelength band of a red light and image data of the near-infrared band. Moreover, after plant grows to a certain extent, analysis of a vegetation index called green normalized difference vegetation index (GNDVI) is effectively used for understanding the change in plant accurately. When GNDVI is calculated, it is necessary to acquire image data of a wavelength band of green light and image data of the near-infrared band. Furthermore, as for rice, wheat, and the like, analysis of NDVI is effectively used for understanding the change in these plants in the harvest time accurately.

As described above, since the type of a vegetation index to be analyzed is different depending on the type of plant and a growth stage, the imaging apparatus 100 according to the present embodiment capable of extracting wavelengths tunably is effectively used for analyzing data after imaging. Since the half-width value of a signal used for analyzing the vegetation index is relatively as large as approximately 50 to 100 [nm] and the imaging apparatus 100 can perform processing using approximately several to several tens of types of filters, it is possible to extract wavelengths tunably while maintaining a resolution.

Here, the present embodiment is not limited to the above description. For example, the imaging apparatus 100 may not be mounted on the UAV 20. Moreover, the target of imaging by the imaging apparatus 100 is not limited to vegetation. For example, the imaging apparatus 100 may be mounted on a vehicle such as an artificial satellite or a tractor. Moreover, the target of imaging by the imaging apparatus 100 may be a structure such as a building or a bridge which is a target of infrastructure inspection and may be an inspection target or the like of factory automation (FA). Moreover, the splitter may split incident light into light beams of wavelengths such as short-wave infrared (SWIR), mid-wave infrared (MWIR), or long-wave infrared (LWIR) as well as visible light and near-infrared light. In this case, the configuration of the splitter or the detector may be changed appropriately depending on light to be split.

2.2. Configuration Example

In the above description, an overview of the first embodiment according to the present disclosure has been described. Next, a configuration example of an apparatus according to the present embodiment will be described.

Figure 6A:
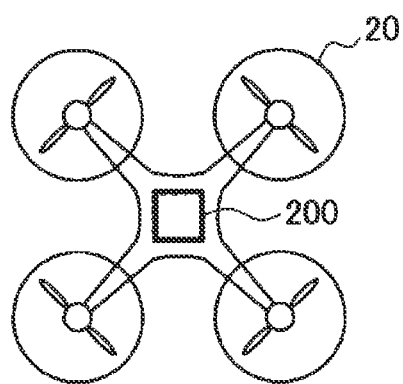
FIGS. 6A and 6B are diagrams illustrating a configuration example of a UAV 20 according to a first embodiment.
Figure 6B:
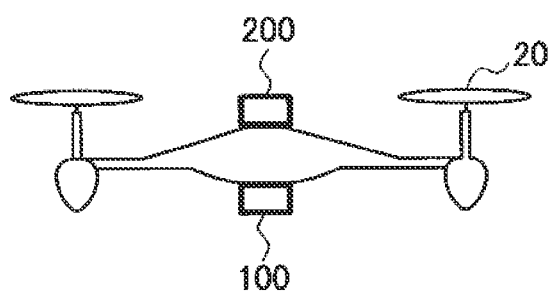

First, a configuration example of the UAV 20 used in the present embodiment will be described with reference to FIGS. 6A and 6B. FIG. 6A is a diagram when the UAV 20 is seen from the top, and FIG. 6B is a diagram when the UAV 20 is seen from a horizontal direction. As illustrated in FIGS. 6A and 6B, the UAV 20 includes the imaging apparatus 100 provided on the lower part thereof in such an aspect that the ground can be imaged and a spectroscope 200 provided in such an aspect that the upper part thereof is radiated with light emitted from the sun (a light source). Here, the shape of the UAV 20 and the installation aspect of the imaging apparatus 100 and the spectroscope 200 are not limited to the example of FIGS. 6A and 6B.

Figure 7:
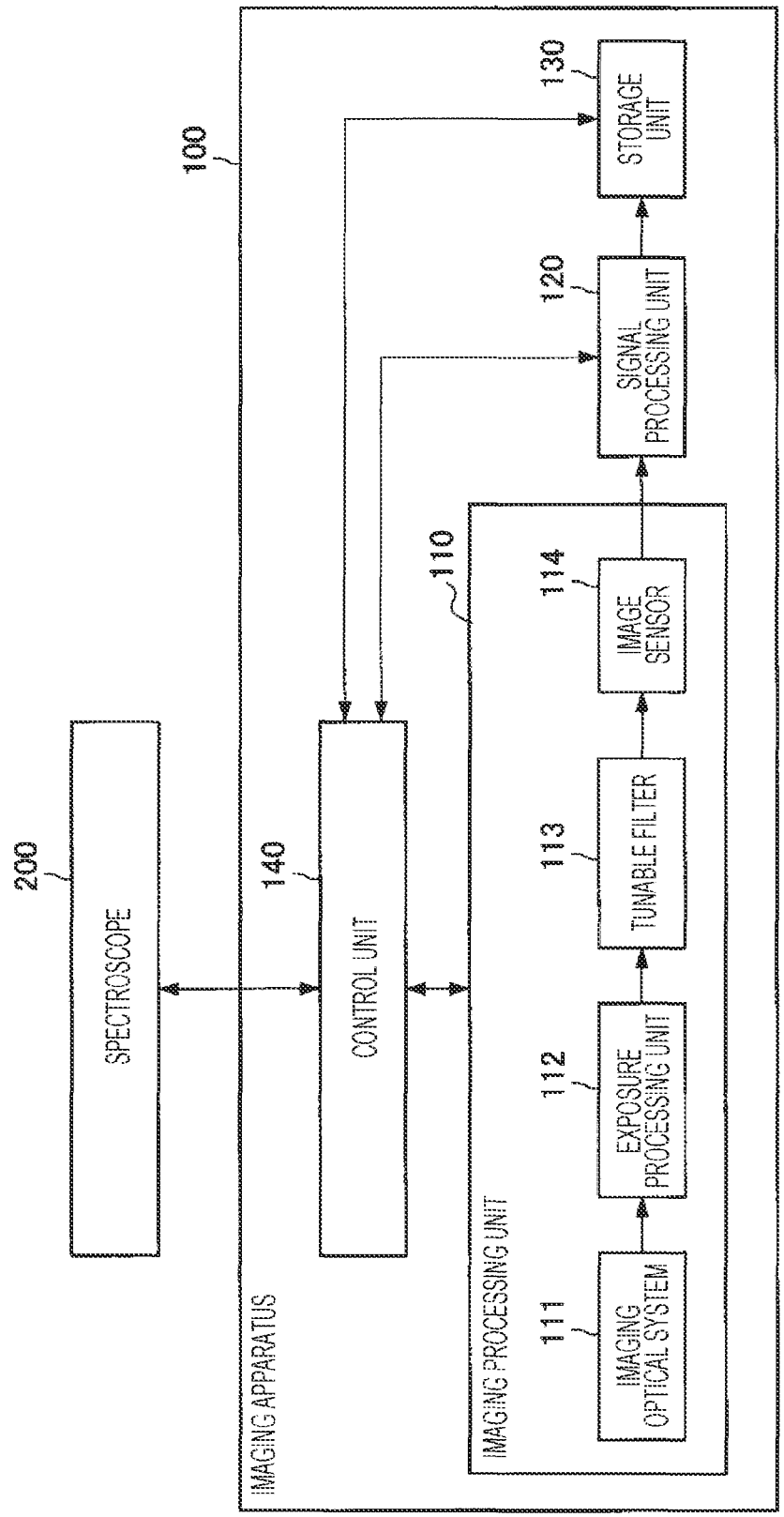
FIG. 7 is a block diagram illustrating a configuration example of the imaging apparatus 100 according to the first embodiment.

Next, a configuration example of the imaging apparatus 100 will be described with reference to FIG. 7. As illustrated in FIG. 7, the imaging apparatus 100 includes an imaging processing unit 110, a signal processing unit 120, a storage unit 130, and a control unit 140.

The imaging processing unit 110 is configured to perform overall imaging processing, and as illustrated in FIG. 7, includes the imaging optical system 111, an exposure processing unit 112, the tunable filter 113, and the image sensor 114.

The imaging optical system 111 includes an optical element used during imaging. As described with reference to FIGS. 3 and 5, the imaging optical system 111 includes the imaging optical system 111 including a lens that receives incident light and the dichroic filter or the like functioning as a splitter that splits the incident light into pieces of light of two wavelength bands. However, the configuration of the imaging optical system 111 is not limited thereto. The incident light is guided to the exposure processing unit 112 on the rear stage via the imaging optical system 111.

The exposure processing unit 112 is configured to perform processing related to exposure. More specifically, the exposure processing unit 112 starts and stops exposure by controlling opening and closing of a shutter or an aperture (IRIS) on the basis of a control signal from the control unit 140. Here, a mechanism for exposure processing included in the exposure processing unit 112 is not particularly limited.

As described with reference to FIGS. 2A and 2B, the tunable filter 113 is a filter in which a plurality of filters having different spectral characteristics are arranged periodically in an array form, and each filter has spectral characteristics of transmitting wide-band light.

The image sensor 114 is an imaging element such as a charge-coupled device (CCD) sensor or a complementary MOS (CMOS), for example, and is configured to acquire image data corresponding to light incident on a light receiving surface by outputting a signal having strength corresponding to the amount of light received for respective pixels that form the light receiving surface.

The tunable filter 113 and the image sensor 114 on the front stage form a detector that outputs a signal from which wavelengths can be extracted tunably. In the present embodiment, a number of detectors formed by the tunable filter 113 and the image sensor 114, basically corresponding to the number of splits of the incident light is provided. Here, the type of the image sensor 114 is not particularly limited. Moreover, the image sensor 114 may output measurement values or the like (for example, measured luminance values or the like) which are not visualized as an image as well as image data.

The signal processing unit 120 also functions as an acquiring unit that acquires signals output by two or more detectors (the tunable filter 113 and the image sensor 114) having detected the split light beams and is configured to perform various signal processings using the signals. For example, the signal processing unit 120 can generate multi-spectrum images by performing demosaic processing, inverse matrix operation processing, and the like with respect to the image data output by the image sensor 114. Here, demosaic processing may be processing of collecting image data of respective pixels simply and may be processing of interpolating defective pixels using the surrounding pixels. The signal processing unit 120 can make multi-spectrum images smoother by performing the latter demosaic processing. Moreover, the signal processing unit 120 can reduce the load of signal processing by performing the former demosaic processing (processing of collecting image data of respective pixels simply). Here, demosaic processing is not necessary but may be omitted appropriately depending on the image data acquired. Furthermore, the signal processing unit 120 can extract image data of a desired wavelength band using multi-spectrum images.

Moreover, the signal processing unit 120 can output the spectral characteristics of vegetation which is a subject. More specifically, since sunlight is incident directly on the spectroscope 200, when $L(\lambda)$ (a value related to spectral characteristics of emission light) is the spectral characteristics of sunlight and $S(\lambda)$ is the spectral characteristics of the spectroscope 200, the output S OUT$(\lambda)$ of the spectroscope 200 is represented by Equation 1 below.

[Math. 1]

$$S\_OUT(\lambda) = L(\lambda) \times S(\lambda) \quad \text{(Equation 1)}$$

Moreover, the signal processing unit 120 calculates the spectral characteristics $L(\lambda)$ of sunlight using Equation 2 below acquired by modifying Equation 1.

[Math. 2]

$$L(\lambda) = \frac{S\_OUT(\lambda)}{S(\lambda)} \quad \text{(Equation 2)}$$

Moreover, since sunlight reaches the imaging apparatus 100 after being reflected from plant, when $P(\lambda)$ (a value related to spectral characteristics of reflection light) is the spectral characteristics of reflectance of plant and $C(\lambda)$ is the spectral characteristics (the spectral characteristics of the tunable filter 113 and the image sensor 114) of the imaging apparatus 100, the output C OUT$(\lambda)$ of the imaging apparatus 100 is represented by Equation 3 below.

[Math. 3]

$$C\_OUT(\lambda) = L(\lambda) \times P(\lambda) \times C(\lambda) \quad \text{(Equation 3)}$$

The signal processing unit 120 calculates the spectral characteristics $P(\lambda)$ of reflectance of plant using Equation 4 below acquired by modifying Equation 3. In this case, the signal processing unit 120 substitutes the spectral characteristics $L(\lambda)$ of sunlight calculated using Equation 2 above into Equation 4.

[Math. 4]

$$P(\lambda) = \frac{C\_OUT(\lambda)}{L(\lambda) \times C(\lambda)} \quad \text{(Equation 4)}$$

That is, it can be said that the signal processing unit 120 calculates the spectral characteristics $P(\lambda)$ of reflectance of plant using Equation 5 below on the basis of Equations 1 to 4 above.

[Math. 5]

$$P(\lambda) = \frac{C\_OUT(\lambda) \times S(\lambda)}{S\_OUT(\lambda) \times C(\lambda)} \quad \text{(Equation 5)}$$

The signal processing unit 120 calculates the spectral characteristics $P(\lambda)$ of reflectance of plant with respect to two or more detectors (the tunable filter 113 and the image sensor 114) on which light after splitting is incident. For example, the signal processing unit 120 calculates $P(\lambda)$ for each of light of the visible wavelength (approximately 750 [nm]) or smaller and light of wavelengths longer than the visible wavelength.

In this manner, since incident light is split into pieces of light of two or more wavelength bands by the splitter and light is detected by a number of detectors (the tunable filter 113 and the image sensor 114) corresponding to the number of splits, the signal processing unit 120 can further decrease the half-width value for the spectral characteristics $P(\lambda)$ of reflectance of plant and improve the resolution.

Figure 8:
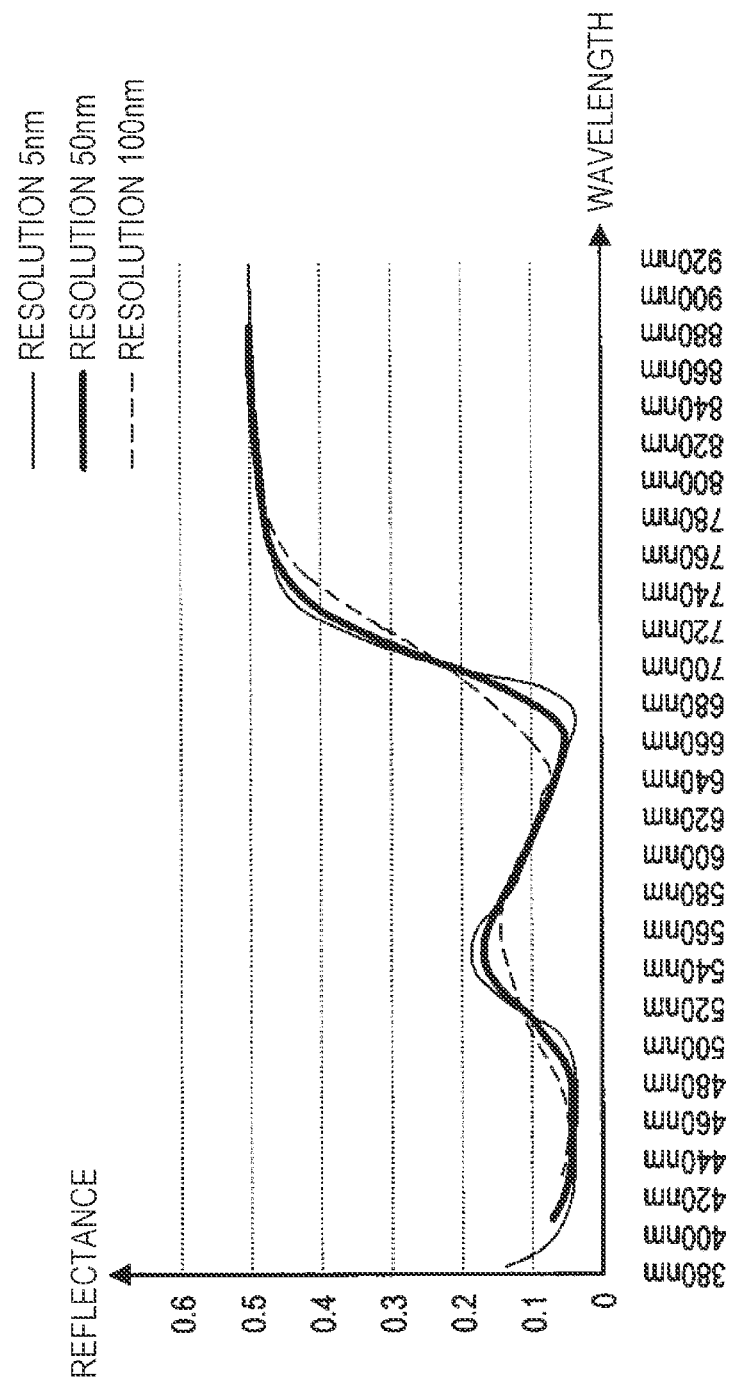
FIG. 8 is a diagram for describing the effects of the present disclosure.

FIG. 8 illustrates the spectral characteristics $P(\lambda)$ of reflectance of hydrangea when the resolution is 5 [nm], 50 [nm], and 100 [nm], respectively. As illustrated in FIG. 8, an abrupt change in $P(\lambda)$ occurs at approximately 700 [nm]. With the present disclosure, the signal processing unit 120 can further improve the resolution (for example, the resolution approaches 5 [nm]) and can reproduce the abrupt change in $P(\lambda)$ at approximately 700 [nm].

Moreover, the signal processing unit 120 calculates various vegetation indices using the spectral characteristics $P(\lambda)$ of reflectance of plant calculated by the above-described processing. Here, the type of a vegetation index calculated by the signal processing unit 120 is not particularly limited. For example, the signal processing unit 120 can calculate a vegetation index such as a normalized difference vegetation index (NDVI), a green normalized difference vegetation index (GNDVI), a photochemical reflectance index (PRI), or a sun-induced fluorescence (SIF).

The storage unit 130 is configured to store various pieces of information. For example, the storage unit 130 can store the multi-spectrum images, the spectral characteristics $P(\lambda)$ of reflectance of plant, various vegetation indices, or the like output by the signal processing unit 120. Here, the information stored in the storage unit 130 is not limited to these examples. For example, the storage unit 130 can store programs, parameters, and the like used by the respective components of the imaging apparatus 100.

The control unit 140 is configured to control overall processing performed by the imaging apparatus 100 in an integrated manner. For example, the control unit 140 can control activation and stopping of imaging processing of the imaging processing unit 110, the signal processing of the signal processing unit 120, and the like. In this case, the control unit 140 also controls, for example, exposure of the exposure processing unit 112 appropriately according to the spectral sensitivity of the tunable filter 113 and the image sensor 114 or the like. Moreover, the control unit 140 can realize the signal processing described above by acquiring spectral data acquired by the spectroscope 200 dispersing the light (for example, sunlight) emitted from a light source and providing the light to the signal processing unit 120. Here, the content of the control performed by the control unit 140 is not limited to these examples.

The spectroscope 200 is configured to generate spectral data by dispersing light (for example, sunlight) emitted from a light source. More specifically, the spectroscope 200 includes various optical elements such as a grating (a diffractive element) or a prism (a refractive element) and disperses the light emitted from the light source using these elements and generates spectral data indicating the intensity of light after the dispersion. The optical elements included in the spectroscope 200 and a method of dispersion are not particularly limited.

Hereinabove, a configuration example of the imaging apparatus 100 (and the spectroscope 200) has been described. Here, the configuration described with reference to FIG. 7 is an example only, and the configuration of the imaging apparatus 100 is not limited to the example. For example, in the example illustrated in FIG. 7, processings ranging from imaging processing to signal processing are completed within the imaging apparatus 100, some or all of these processings may be realized by an external apparatus.

Figure 9:
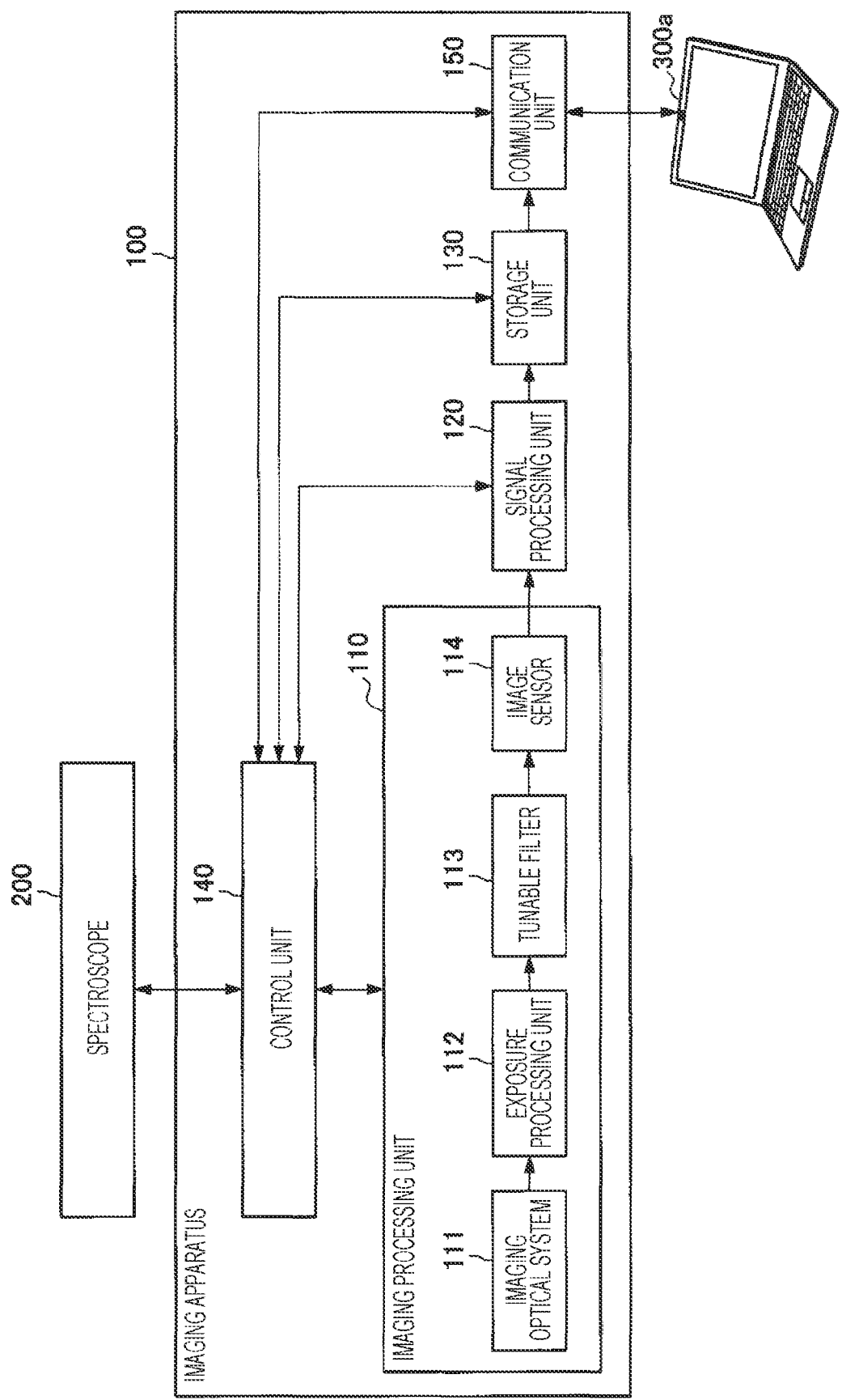
FIG. 9 is a block diagram illustrating a configuration example of the imaging apparatus 100 according to the first embodiment.

For example, some or all functions of the signal processing unit 120 may be realized by an external apparatus. More specifically, as illustrated in FIG. 9, the function of the signal processing unit 120 may be realized by an information processing apparatus 300a (for example, a personal computer (PC) or the like) capable of communicating with the imaging apparatus 100. In this case, the signal processing unit 120 stores data in the storage unit 130 without performing some or all of processings described above. Moreover, the imaging apparatus 100 further includes a communication unit 150 that performs communication with the information processing apparatus 300a, and the communication unit 150 transmits data stored in the storage unit 130 to the information processing apparatus 300a. Here, a communication method, the type of communication lines, or the like used for the communication between the communication unit 150 and the information processing apparatus 300a is not particularly limited. Moreover, in order to secure a communication band, the communication unit 150 may transmit data compressed by a predetermined lossless compression method to the information processing apparatus 300a.

Moreover, the information processing apparatus 300a calculates the spectral characteristics $P(\lambda)$ of reflectance of plant and calculates a vegetation index by performing the above-described signal processing using the data received from the imaging apparatus 100. Since the processing performance of the imaging apparatus 100 is sometimes lower than that of the information processing apparatus 300a due to the demand for reduction in size or the like, signal processing with a higher processing load is realized by the information processing apparatus 300a whereby the speed or the efficiency of entire processing can be improved. Here, the content of processing performed by the imaging apparatus 100 and the information processing apparatus 300a is not limited to the above. Moreover, the content of processing allocated to the imaging apparatus 100 and the information processing apparatus 300a is not particularly limited.

Figure 10:
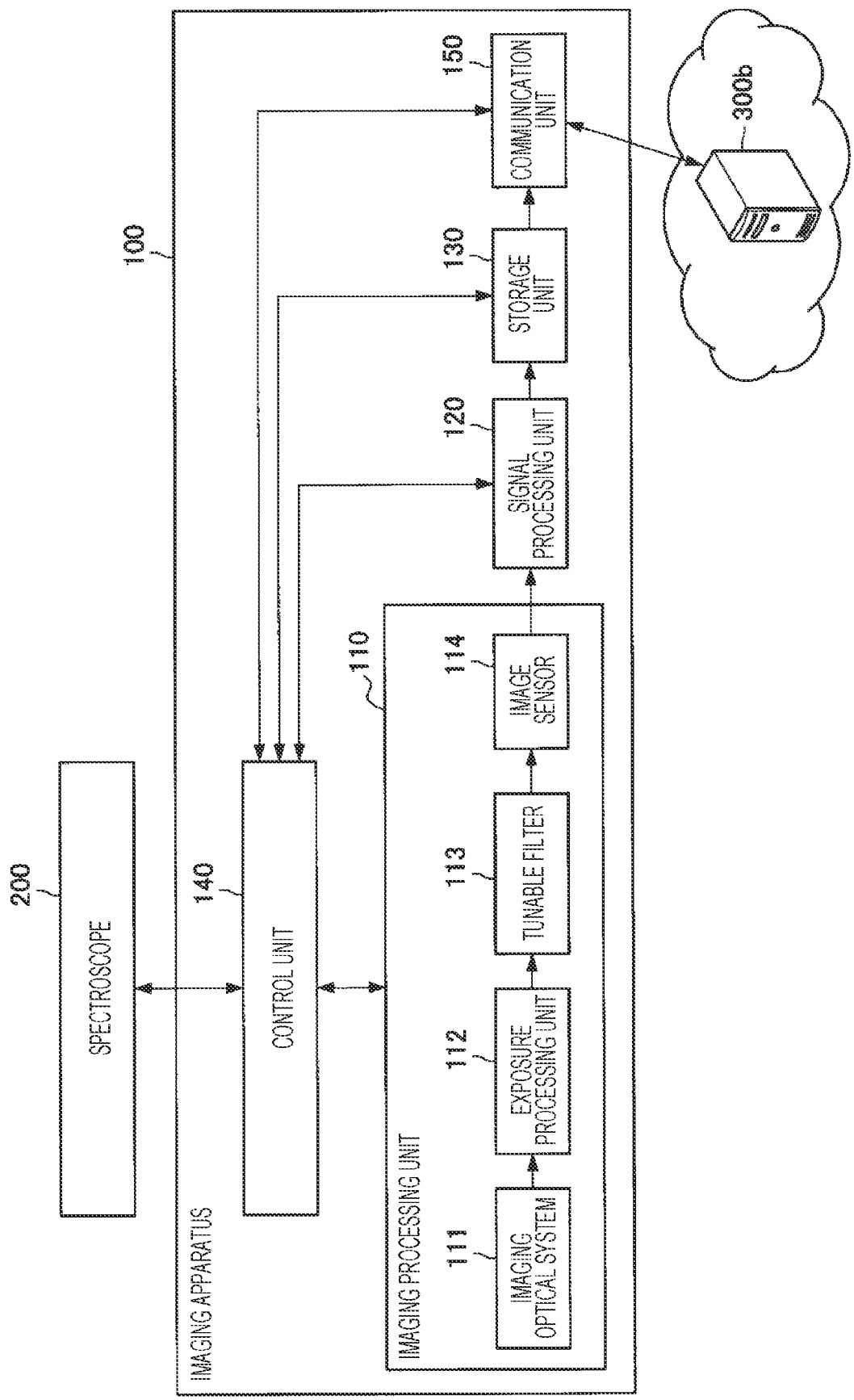
FIG. 10 is a block diagram illustrating a configuration example of the imaging apparatus 100 according to the first embodiment.

Moreover, as illustrated in FIG. 10, the communication unit 150 of the imaging apparatus 100 rather than the information processing apparatus 300a may communicate with a cloud server 300b provided on a cloud network whereby some or all functions of the signal processing unit 120 may be realized by the cloud server 300b. In this way, the speed or the efficiency of the entire processing can be improved further. Moreover, the cloud server 300b may acquire image data or the like via another information processing apparatus that communicates with the imaging apparatus 100 rather than communicating with the imaging apparatus 100. Here, it is to be noted that an apparatus (for example, the imaging apparatus 100, the information processing apparatus 300a, and the cloud server 300b) including a configuration that realizes some or all functions of the signal processing unit 120 functions as a "signal processing apparatus".

2.3. Example of Flow of Signal Processing

In the above description, a configuration example of an apparatus according to the present embodiment has been described. Next, an example of the flow of signal processing according to the present embodiment will be described with reference to FIG. 11. As described above, the information processing apparatus 300a or the cloud server 300b which is an external apparatus can realize the function of the signal processing unit 120 of the imaging apparatus 100. However, a case in which the signal processing unit 120 of the imaging apparatus 100 realizes all signal processings will be described as an example.

In step S1000, the signal processing unit 120 of the imaging apparatus 100 acquires spectral data generated by the spectroscope 200 from the control unit 140 and acquires image data from the image sensor 114. In step S1004, the signal processing unit 120 processes the spectral data. More specifically, the signal processing unit 120 calculates the spectral characteristics $L(\lambda)$ of sunlight using Equation 2 above.

In step S1008, the signal processing unit 120 processes image data. More specifically, the signal processing unit 120 calculates the spectral characteristics $P(\lambda)$ of reflectance of plant using Equation 4 above. In this case, the signal processing unit 120 substitutes the spectral characteristics $L(\lambda)$ of sunlight calculated in step S1004 into Equation 4.

In step S1012, the signal processing unit 120 calculates various vegetation indices using the spectral characteristics $P(\lambda)$ of reflectance of plant whereby a series of signal processings ends. For example, the signal processing unit 120 calculates NDVI, GNDVI, and the like using $P(\lambda)$.

Figure 11:
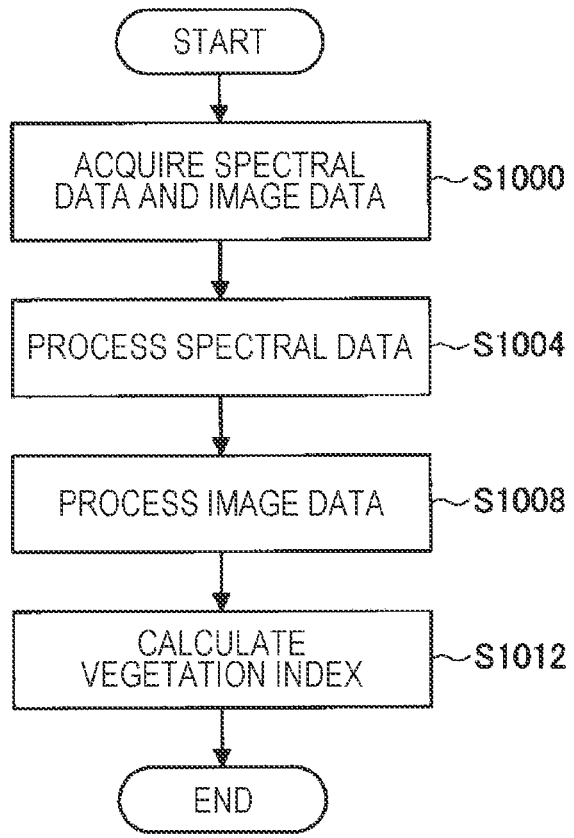
FIG. 11 is a flowchart illustrating a signal processing example.

Here, the respective steps of the flowchart illustrated in FIG. 11 are not necessarily processed in a time-series order according to the described order. That is, the respective steps of the flowchart may be processed in an order different from the described order and may be processed in parallel.

3. SECOND EMBODIMENT

In the above description, the first embodiment of the present disclosure has been described. Next, a second embodiment of the present disclosure will be described.

In the first embodiment according to the present disclosure, the spectral characteristics $L(\lambda)$ of sunlight used for calculating the spectral characteristics $P(\lambda)$ of reflectance of plant are acquired by the spectroscope 200. In the second embodiment of the present disclosure, the imaging apparatus 100 is used as the spectroscope 200.

Figure 12A:
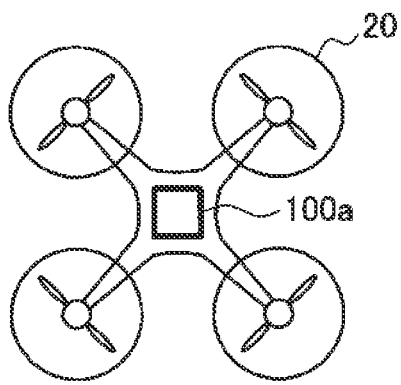
FIGS. 12A and 12B are diagrams illustrating a configuration example of a UAV 20 according to a second embodiment.
Figure 12B:
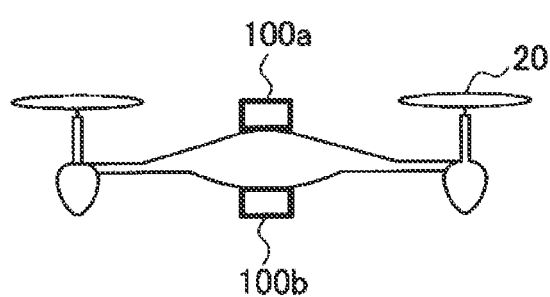

More specifically, as illustrated in FIGS. 12A and 12B, the UAV 20 includes an imaging apparatus 100a used as the spectroscope 200 in such an aspect that the upper part thereof is radiated with sunlight. Moreover, the UAV 20 includes an imaging apparatus 100b provided on the lower part thereof in such a form that the ground can be imaged similarly to the first embodiment. Here, the shape of the UAV 20 according to the present embodiment and the installation aspect of the imaging apparatus 100a and the imaging apparatus 100b is not limited to the example of FIGS. 12A and 12B.

Next, a configuration example of the imaging apparatus 100a and the imaging apparatus 100b according to the present embodiment will be described with reference to FIG. 13. As illustrated in FIG. 13, the imaging apparatus 100a used as the spectroscope 200 includes an imaging processing unit 110a, a signal processing unit 120a, a storage unit 130a, and a control unit 140a. Moreover, the imaging processing unit 110a includes an imaging optical system 111a, an exposure processing unit 112a, a tunable filter 113a, and an image sensor 114a.

The imaging optical system 111a includes a diffuser instead of the lens of the imaging optical system 111 according to the first embodiment and includes a dichroic filter that functions as a splitter on the rear stage thereof. Here, an element other than the diffuser may be used as long as the element is an optical element capable of diffusing incident light. The exposure processing unit 112a, the tunable filter 113a, and the image sensor 114a are similar to those of the imaging apparatus 100 according to the first embodiment, and the description thereof will be omitted.

The signal processing unit 120a can calculate the spectral characteristics $L(\lambda)$ of sunlight using the outputs from two or more detectors (the tunable filter 113 and the image sensor 114). For example, the signal processing unit 120a calculates $L(\lambda)$ for each of light of the visible wavelength (approximately 750 [nm]) or smaller and light of wavelengths longer than the visible wavelength. Here, processing of calculating $L(\lambda)$ may be performed by the signal processing unit 120b of the imaging apparatus 100b.

The storage unit 130a stores the spectral characteristics $L(\lambda)$ of sunlight and the like, output by the signal processing unit 120a. The control unit 140a provides the spectral characteristics $L(\lambda)$ of sunlight and the like output by the signal processing unit 120a to the imaging apparatus 100b.

Hereinabove, the configuration example of the imaging apparatus 100a has been described. Here, the configuration described with reference to FIG. 13 is an example only, and the configuration of the imaging apparatus 100a is not limited to the example. On the other hand, the configuration of the imaging apparatus 100b is similar to the configuration of the imaging apparatus 100 according to the first embodiment described with reference to FIG. 7, and the description thereof will be omitted. Moreover, some or all functions of the imaging apparatus 100a may be realized by the imaging apparatus 100b, and conversely, some or all functions of the imaging apparatus 100b may be realized by the imaging apparatus 100a. Furthermore, in the present embodiment, as described above with reference to FIGS. 9 and 10, some or all processings ranging from imaging processing to the signal processing may be realized by an external apparatus (for example, the information processing apparatus 300a or the cloud server 300b).

Next, signal processing related to the present embodiment will be described with reference to FIG. 11. As for "spectral data processing" of step S1004, $L(\lambda)$ is calculated for each of light of the visible wavelength (approximately 750 [nm]) or smaller and light of wavelengths longer than the visible wavelength. Moreover, in "image data processing" of step S1008, the signal processing unit 120b uses $L(\lambda)$ for light of the visible wavelength (approximately 750 [nm]) or smaller when calculating $P(\lambda)$ for the light of the visible wavelength (approximately 750 [nm]) or smaller and uses $L(\lambda)$ for light of wavelengths longer than the visible wavelength when calculating $P(\lambda)$ for the light of wavelengths longer than the visible wavelength. Since the other processings are similar to those of the process flow according to the first embodiment, the description thereof will be omitted.

Figure 14:
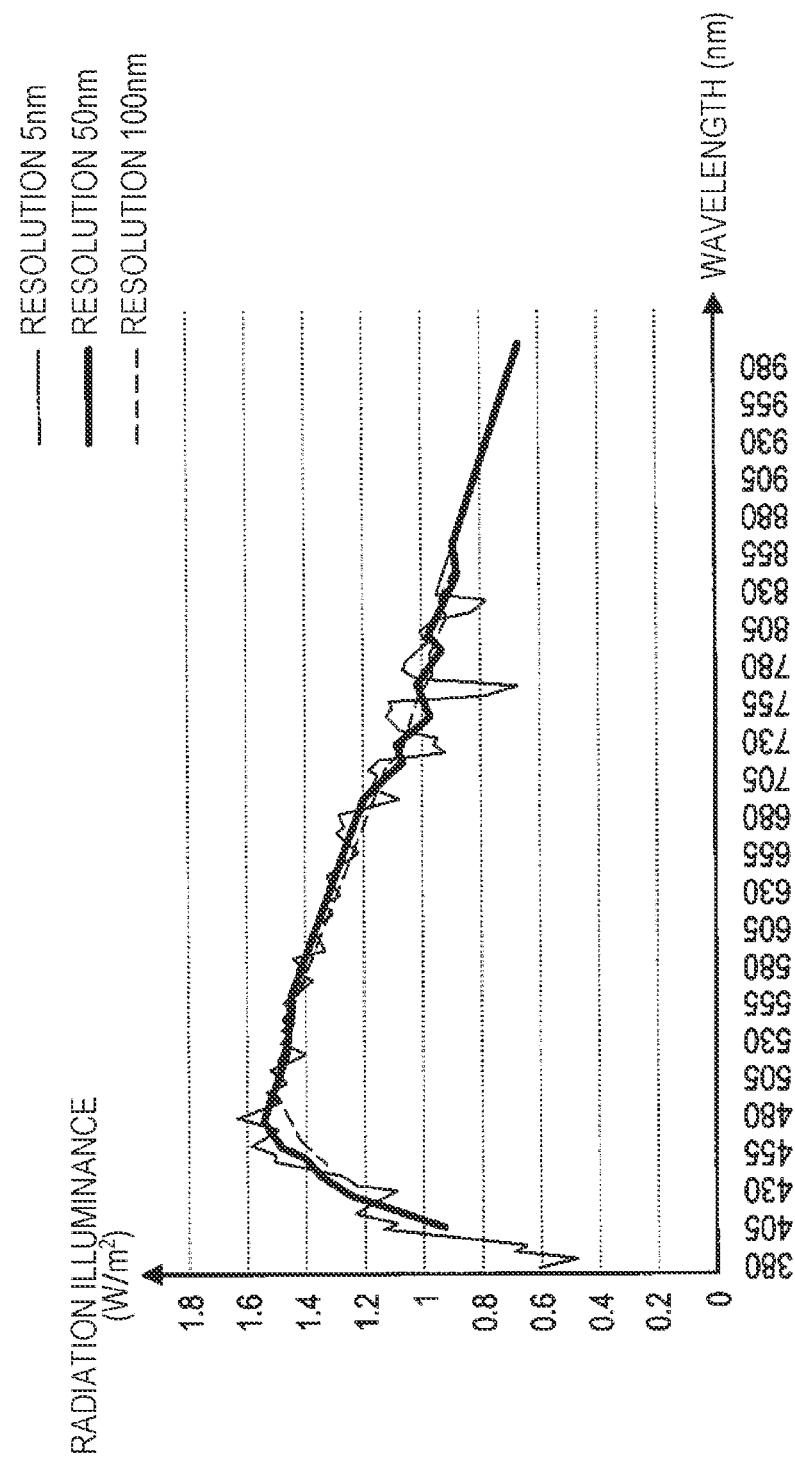
FIG. 14 is a diagram illustrating a specific example of spectral characteristics of sunlight acquired by the imaging apparatus 100a according to the second embodiment.
Figure 15:
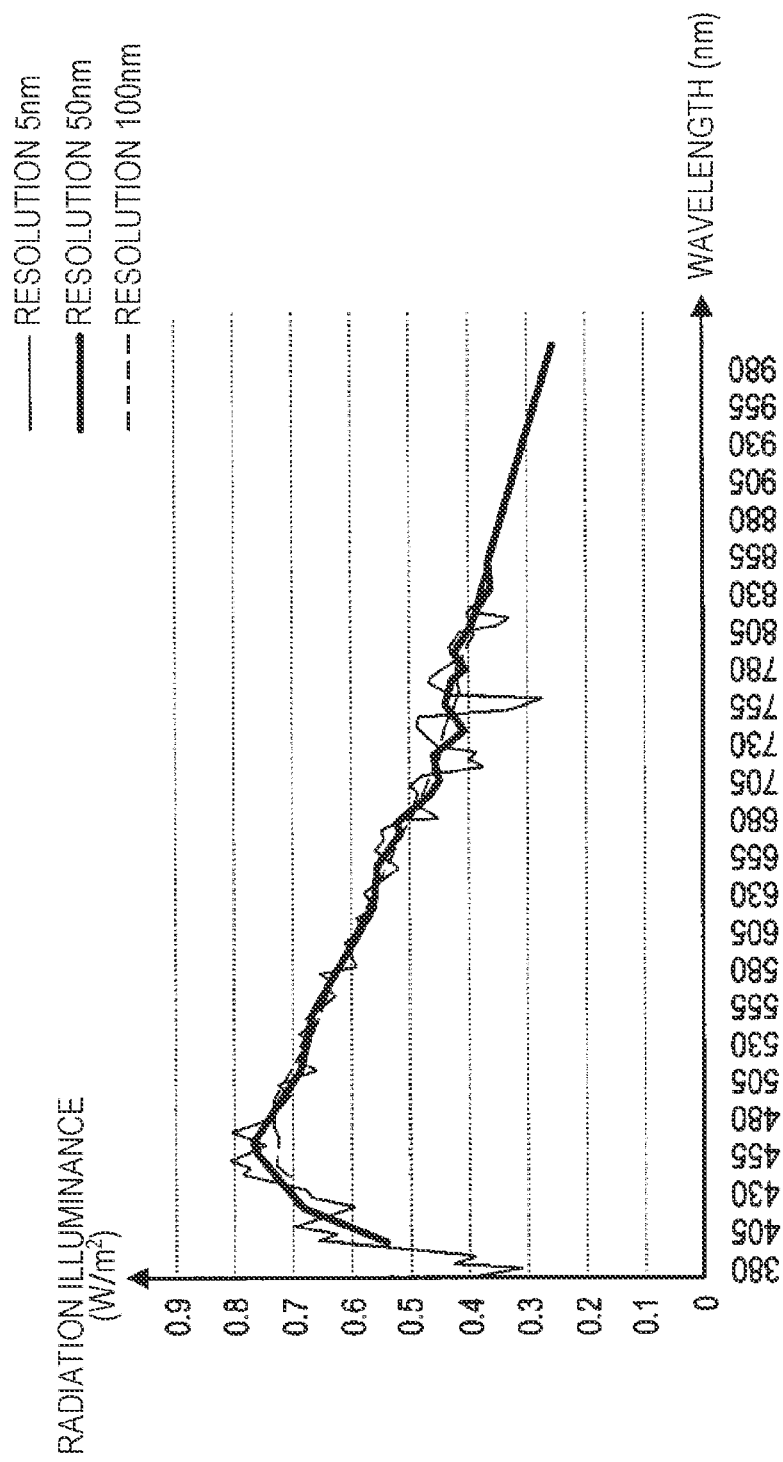
FIG. 15 is a diagram illustrating a specific example of spectral characteristics of sunlight acquired by the imaging apparatus 100a according to the second embodiment.
Figure 16:
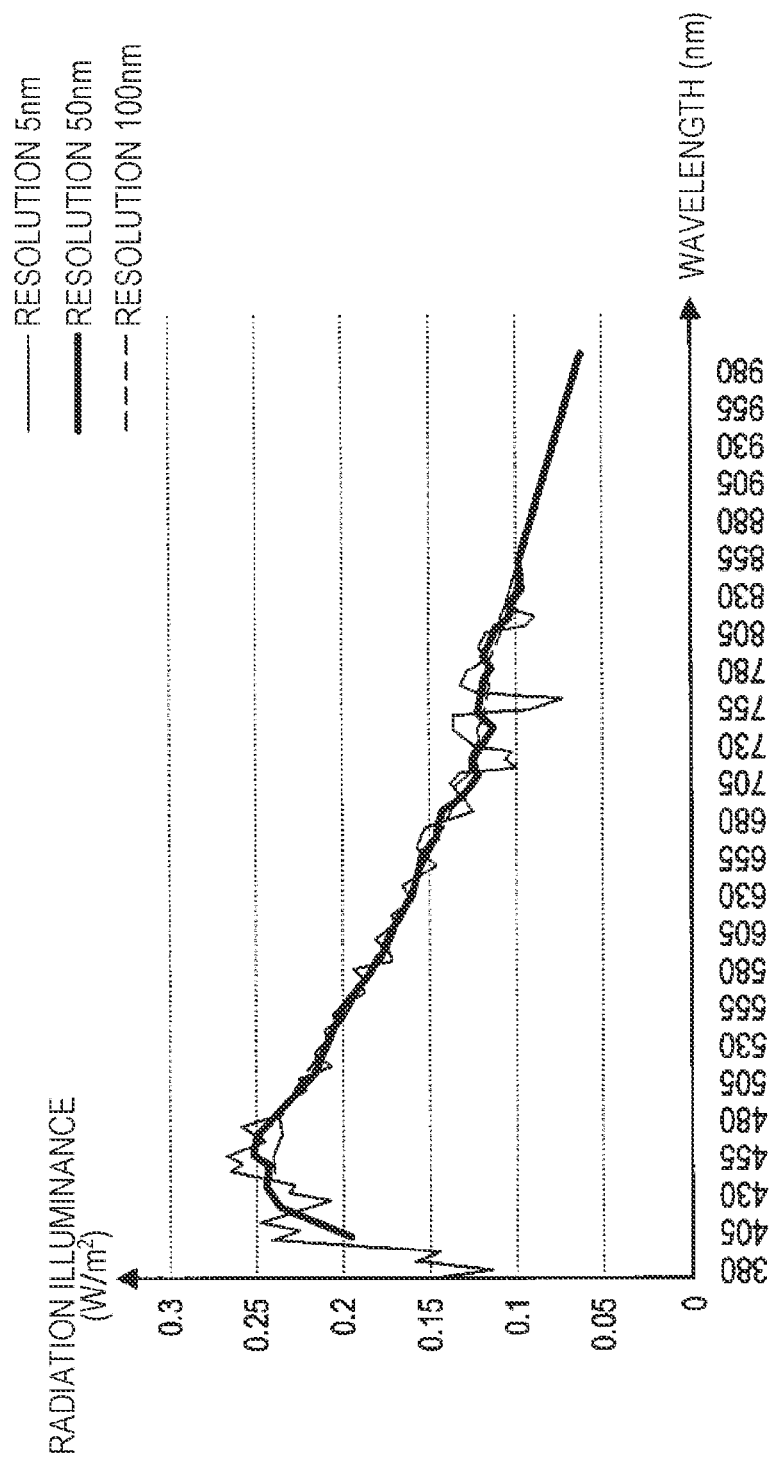
FIG. 16 is a diagram illustrating a specific example of spectral characteristics of sunlight acquired by the imaging apparatus 100a according to the second embodiment.

According to the second embodiment of the present disclosure, a frequency range in which the spectral characteristics of sunlight can be reproduced is increased. Particularly, when the tunable filter 113 illustrated in FIG. 5 (that is, the tunable filter 113 specialized to a wavelength band of light after splitting) is used, a frequency range in which the spectral characteristics of sunlight can be reproduced is increased particularly. For example, FIGS. 14 to 16 illustrate the spectral characteristics of sunlight when a color temperature is 6500 [K], 7000 [K], and 7500 [K], respectively, and as illustrated in these drawings, an abrupt change around approximately 450 [nm] is reproduced with a higher resolution. Here, the tunable filters 113 illustrated in FIG. 3 (that is, the tunable filters 113 having approximately the same spectral characteristics) may be used as the tunable filters 113 used for splitting incident light. Moreover, in the present embodiment, the signal processing unit 120b can further decrease the half-width value for the spectral characteristics $P(\lambda)$ of reflectance of plant and improve the resolution.

4. APPLICATION EXAMPLE

In the above description, the second embodiment of the present disclosure has been described. Next, an application example of the present disclosure will be described. The technology according to the present disclosure can be applied to various apparatuses or systems. For example, the technology according to the present disclosure may be applied to a medical imaging apparatus including a medical microscope, a medical endoscope, or the like and a medical imaging system (a medical microscope system, a medical endoscope system, or the like) including these apparatuses.

4.1. Application Example to Medical Imaging Apparatus

Figure 17:
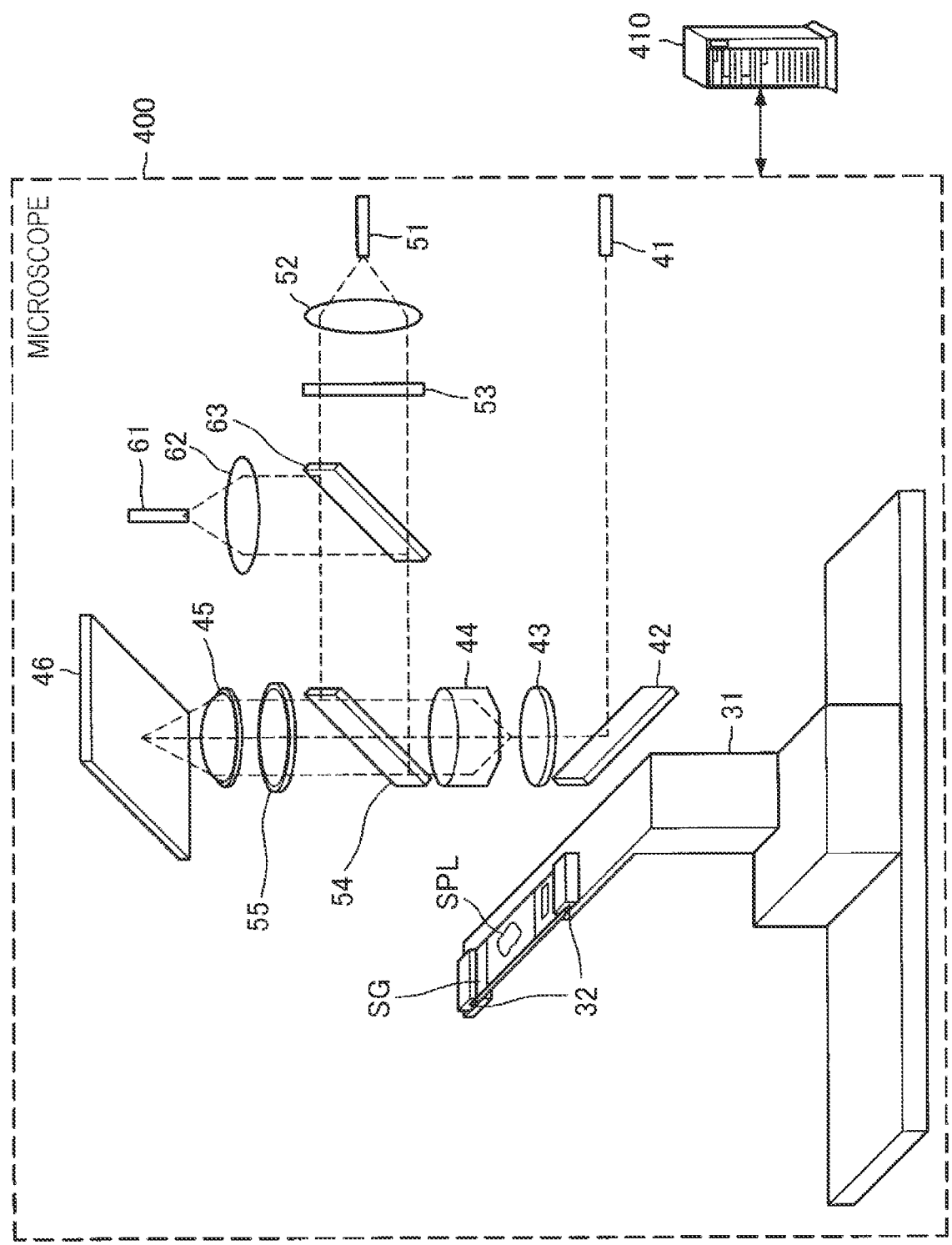
FIG. 17 is a diagram illustrating an example when the technology according to the present disclosure is applied to a medical imaging apparatus.

Here, an example when the technology according to the present disclosure is applied to a medical imaging apparatus will be described with reference to FIG. 17. As illustrated in FIG. 17, a medical imaging apparatus to which the present disclosure is applied includes a microscope 400 and a data processing unit 410.

The microscope 400 according to this application example includes a splitter that splits incident light into pieces of light of two or more wavelength bands and two or more detectors that detect the pieces of light of two or more wavelength bands and output signals from which wavelengths can be extracted tunably by post-processing. More specifically, the microscope 400 includes an image sensor 46 which functions as a detector and has a tunable filter on the front stage thereof. Here, it is to be noted that only one image sensor 46 functioning as a detector is illustrated in FIG. 17, and the other image sensors 46 are not illustrated for the sake of convenience. Moreover, it is to be noted that a dichroic filter 54 functions as a splitter. That is, incident light is split into light beams of two or more wavelength bands by the dichroic filter 54, and the laser beams after splitting are detected by different image sensors 46. Here, the aspect of the splitter and the detector included in the microscope 400 is not particularly limited.

The data processing unit 410 according to this application example can use the data output from two or more detectors for different uses. For example, an aspect in which the data processing unit 410 performs focusing using image data of any one of two or more detectors and then, for example, performs imaging using image data of the other detector may be considered. Here, a use aspect of two or more detectors is not limited thereto. Moreover, a splitting point of the splitter is not limited to approximately 750 [nm] as described above and is determined depending on an imaging target.

In related art, it takes a considerable time in focusing since users, for example, replace filters in order to perform focusing using image data of a specific wavelength band. On the other hand, in this application example, as described above, the microscope 400 includes a splitter that splits incident light into pieces of light of two wavelength bands and detectors corresponding to the number of splits of the incident light, the data processing unit 410 can perform focusing without replacing filters and perform imaging after focusing. In a medical field, since it is necessary to acquire a large number of pathological images or medical images in a short time, the present disclosure capable of performing focusing and imaging after focusing in a shorter time is useful.

Moreover, the data processing unit 410 can extract images of a desired wavelength band by performing the above-described signal processing with respect to the image data acquired by imaging after focusing. In this way, the user's convenience is improved. In the following description, the details of this application example including the configuration of the microscope 400 will be described.

Moreover, the microscope 400 includes a plurality of light sources and can switch between a bright-field imaging mode and a dark-field imaging mode by controlling these light sources. Here, a bright-field imaging mode is a mode in which a normal illumination light is emitted to a biological sample SPL whereby an entire or partial bright-field image (an entire bright-field image or a partial bright-field image) can be acquired. On the other hand, a dark-field imaging mode is a mode in which light that excites a partial portion of a biological sample SPL is emitted to the biological sample SPL which is partially fluorescently stained whereby a partial fluorescent image (hereinafter also referred to as a "partial bright-field image") of the biological sample SPL can be acquired. Moreover, for either one of the bright-field imaging mode and the dark-field imaging mode, the data processing unit 410 can use the data output from two or more detectors for different uses as described above.

(Details of Configuration of Microscope 400 and the Like)

The microscope 400 has a stage (hereinafter also referred to a movable stage) 31 capable of moving in a parallel direction and an orthogonal direction (x-axis, y-axis, and z-axis directions) with respect to a surface (hereinafter also referred to as a slide arrangement surface) on which a slide SG such as a glass plate is disposed. A slide holder 32 is provided on the slide arrangement surface.

When the slide SG is set, the slide holder 32 moves to a position designated as a set plate (hereinafter this position is also referred to as a slide set position). At the slide set position, the slide SG accommodated in a slide container (not illustrated) is taken out by a slide set mechanism (not illustrated) and is set on the slide holder 32.

Connective tissues such as the blood, epithelial tissues, and a tissue unit, a smear cell, or the like of both tissues are fixed to the slide SG accommodated in the slide container (not illustrated) as the biological sample SPL by a predetermined fixing method and are stained as necessary.

This staining includes fluorescent staining such as fluorescence in-situ hybridization (FISH) or an enzyme antibody technology as well as general staining represented by hematoxylin-eosin (HE) staining papanicolaou staining, or the like.

In fluorescent staining, generally, a fluorescent label (hereinafter also referred to as a comparison marker) to be compared with a fluorescent marker of a probe as well as a fluorescent label (hereinafter also referred to as a fluorescent marker) attached to the probe are used.

The comparison marker has an excitation wavelength different from the excitation wavelength of the fluorescent marker. For example, the comparison marker has an excitation wavelength of approximately 365 [nm] and 4',6-diamidino-2-pheylindole (DAPI) is generally used.

In DAPI, a cell nucleus is used as a target (hereinafter referred to as a comparison target) to be compared with the target of the fluorescent marker.

When the biological sample SPL is imaged, the slide holder 32 is moved to a position (hereinafter also referred to as a microscopic examination position) designated as a microscopic examination place. In this case, a bright-field imaging mode or a dark-field imaging mode is executed.

In the bright-field imaging mode, an illumination light for the biological sample SPL is emitted from a bright-field light source 41. The illumination light is reflected by a reflection mirror 42 and is emitted to the biological sample SPL at the microscopic examination position as light of the visible band via a bright-field filter 43 to reach an objective lens 44.

The objective lens 44 has a low magnification such that an image (hereinafter also referred to as an entire bright-field image) of the entire biological sample SPL is imaged or has a high magnification such that an image (hereinafter also referred to as a partial bright-field image) of a partial portion of the biological sample SPL is imaged.

The microscope 400 magnifies the image of the biological sample SPL acquired via the illumination light using the objective lens 44 and an imaging lens 45 and forms the image on an imaging surface of an image sensor 46 as an entire bright-field image or a partial bright-field image.

In this manner, in the bright-field imaging mode, the microscope 400 can acquire an entire or partial bright-field image (an entire bright-field image or a partial bright-field image) of the biological sample SPL.

Here, in FIG. 17, a dichroic filter 54 and an emission filter 55 that function as a splitter are present in an optical path between the objective lens 44 and the imaging lens 45. However, in the bright-field imaging mode, the dichroic filter 54 and the emission filter 55 are retracted to a position other than the optical path so that the light of the visible band incident from the bright-field filter 43 is not absorbed by or reflected from these filters.

On the other hand, in the dark-field imaging mode, light (hereinafter also referred to as excitation light) that excites both the comparison marker and the fluorescent marker of the probe is emitted from an excitation light source 51. When the excitation light is emitted, the objective lens 44 has a high magnification such that a partial fluorescent image of the biological sample SPL is imaged.

The excitation light emitted from the excitation light source 51 is collimated to rays of parallel light by a collimator lens 52 and light other than the excitation light is removed by an excitation filter 53. The excitation light that passes through the excitation filter 53 is reflected from the dichroic filter 54 and is focused on the microscopic examination position by the objective lens 44.

When the probe is coupled with the comparison target and the target of the biological sample SPL disposed at the microscopic examination position, the comparison marker and the fluorescent marker attached to the probe emit light due to the excitation light. This emission light passes through the dichroic filter 54 via the objective lens 44, and light other than the emission light of the fluorescent body is absorbed by the emission filter 55 to reach the imaging lens 45.

The microscope 400 magnifies the image acquired via the emission of the fluorescent marker and the comparison marker using the objective lens 44 and the imaging lens 45 to form the image on the imaging surface of the image sensor 46 as a partial dark-field image.

In this way, in the dark-field imaging mode, the microscope 400 can acquire a partial fluorescent image (a partial dark-field image) of the sample.

Here, although a dichroic filter 63 is present in an optical path between the excitation filter 53 and the dichroic filter 54 in FIG. 17, the excitation light that passes through the excitation filter 53 passes through the dichroic filter 63.

In addition to the above-mentioned configuration, the microscope 400 has a light source (hereinafter also referred to as a comparison excitation light source) 61 that emits excitation light (hereinafter also referred to as a comparison exclusive excitation light) that puts the comparison marker into an excitation state while leaving the fluorescent marker in a non-excitation state.

The comparison exclusive excitation light is emitted from the comparison excitation light source 61 in focusing processing when a partial dark-field image of the biological sample SPL is acquired.

The comparison exclusive excitation light emitted from the comparison excitation light source 61 is collimated to rays of parallel light by the collimator lens 62 and is reflected from the dichroic filter 63 and the dichroic filter 54 and is focused on the microscopic examination position by the objective lens 44.

When the probe is coupled with the comparison target of the biological sample SPL disposed at the microscopic examination position, the comparison marker attached to the probe emits light due to the comparison exclusive excitation light. This emission light passes through the dichroic filter 54 via the objective lens 44, and light other than the emission light of the fluorescent body is absorbed by the emission filter 55 to reach the imaging lens 45.

The microscope 400 magnifies the image acquired via the emission of the comparison marker using the objective lens 44 and the imaging lens 45 to form the image on the imaging surface of the image sensor 46 as a partial dark-field image.

The data processing unit 410 controls the movable stage 31 so that a focal point is formed in a corresponding sample portion using the partial dark-field image. Moreover, when a focal point is formed in the sample portion, the data processing unit 410 emits excitation light from the excitation light source 51 instead of the comparison excitation light source 61 and stores the partial dark-field image acquired by the excitation light.

As described above, the medical imaging apparatus acquires the partial dark-field image acquired by the comparison exclusive excitation light as a focusing target partial dark-field image and acquires the partial dark-field image acquired by the excitation light as a storage target partial dark-field image.

(Flow of processing) In the above description, the details of the configuration of the microscope 400 and the like have been described. Next, an example of the flow of processings of the medical imaging apparatus will be described with reference to FIG. 18.

In step S1100, the data processing unit 410 arranges the slide holder 32 at the microscopic examination position and arranges the high-magnification objective lens 44 on the optical axis between the dichroic filter 54 and the imaging lens 45. The data processing unit 410 may arrange the other components at a predetermined position.

In step S1104, the data processing unit 410 determines an acquisition target sample portion of the biological sample SPL disposed on the slide holder 32. A method of determining the acquisition target sample portion is not particularly limited, and for example, the acquisition target sample portion may be determined on the basis of a user's designation.

In step S1108, the data processing unit 410 drives the comparison excitation light source 61 to acquire image data of either one of two or more detectors. In step S1112, the data processing unit 410 aligns a focal point in the acquisition target sample portion on the basis of the contrast of a portion of a dark-field image (a partial dark-field image) of the comparison marker in the acquisition target sample portion.

In step S1116, the data processing unit 410 stops driving of the comparison excitation light source 61 and drives the excitation light source 51. In step S1120, the data processing unit 410 acquires a dark-field image of the fluorescent marker in the acquisition target sample portion using a detector different from the detector used for focusing as a recording target partial dark-field image whereby a series of processings ends.

Figure 18:
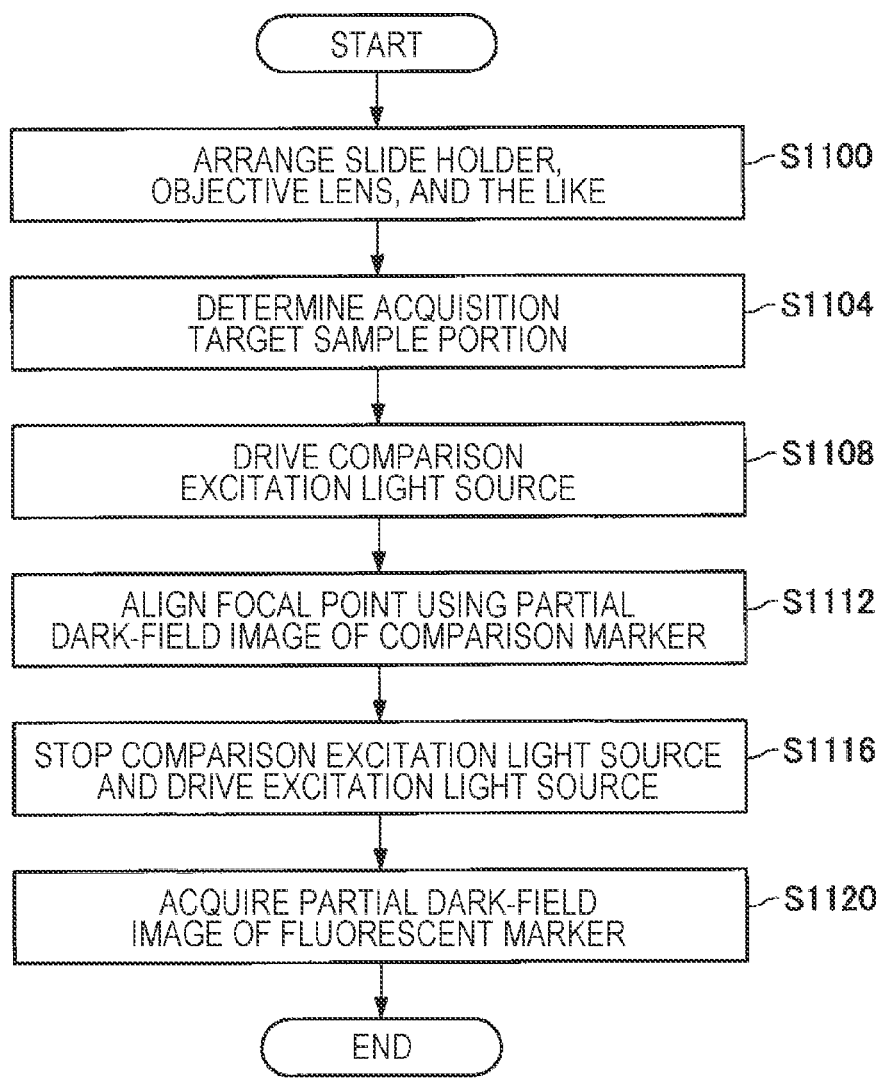
FIG. 18 is a flowchart illustrating an example of the flow of processing of the medical imaging apparatus.

Here, the respective steps of the flowchart illustrated in FIG. 18 are not necessarily processed in a time-series order according to the described order. That is, the respective steps of the flowchart may be processed in an order different from the described order and may be processed in parallel.

In the above description, although an example in which the technology according to the present disclosure is applied to a medical imaging apparatus has been described, an apparatus and a system to which the technology according to the present disclosure is applied are not particularly limited. More specifically, the technology according to the present disclosure may be applied to an arbitrary apparatus other than the medical imaging apparatus.

(4.2. Application example to operating room system)
Next, an example in which the technology according to the present disclosure is applied to an operating room system will be described.

Figure 19:
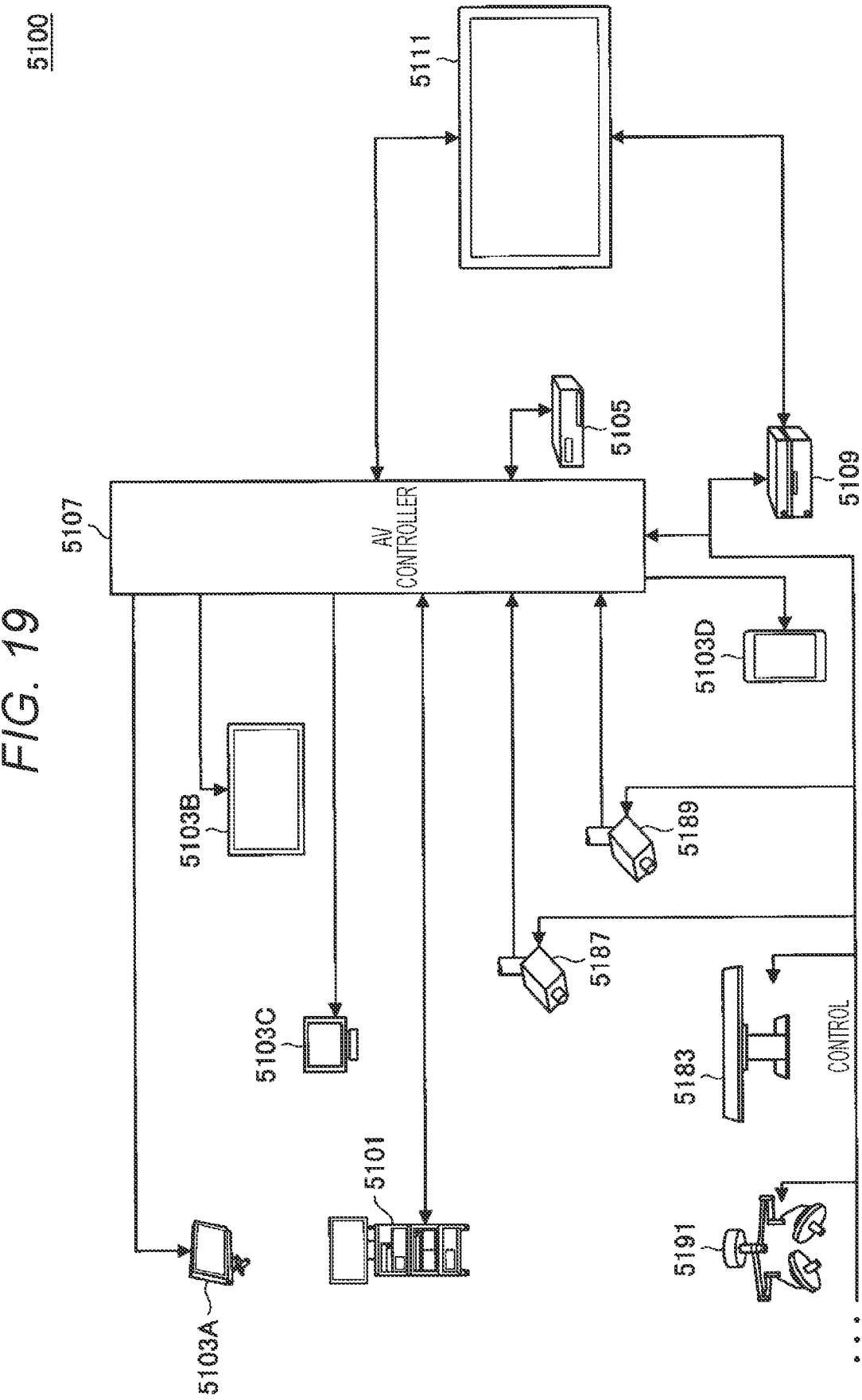
FIG. 19 is a diagram schematically illustrating an entire configuration of an operating room system.

FIG. 19 is a diagram schematically illustrating an overall configuration of an operating room system 5100 to which the technology according to the present disclosure is applied. Referring to FIG. 19, the operating room system 5100 is configured such that an apparatus group installed in an operating room is connected via an audio-visual controller (AV controller) 5107 and an operating room controller 5109 so as to cooperate with each other.

Various apparatuses are installed in an operating room. In FIG. 19, as an example, various apparatus groups 5101 for endoscopic surgery, a ceiling camera 5187 provided on the ceiling of the operating room to image the hands of an operator, a room camera 5189 provided on the ceiling of the operating room to image the view of the entire operating room, a plurality of displays 5103A to 5103D, a recorder 5105, a patient bed 5183, and an illumination 5191 are illustrated.

Here, among these apparatuses, the apparatus group 5101 belongs to an endoscopic surgery system 5113 to be described later and includes an endoscope, a display that displays images acquired by the endoscope, and the like. The respective apparatuses belonging to the endoscopic surgery system 5113 are also referred to as medical apparatuses. On the other hand, the displays 5103A to 5103D, the recorder 5105, the patient bed 5183, and the illumination 5191 are apparatuses provided in the operating room, for example, separately from the endoscopic surgery system 5113. These apparatuses that do not belong to the endoscopic surgery system 5113 are also referred to as non-medical apparatuses. The AV controller 5107 and/or the operating room controller 5109 control the operation of these medical apparatuses and non-medical apparatuses in cooperation.

The AV controller 5107 controls processings related to image display of the medical apparatuses and the non-medical apparatuses in an integrated manner.

Specifically, among the apparatuses included in the operating room system 5100, the apparatus group 5101, the ceiling camera 5187, and the room camera 5189 may be an apparatus (hereinafter also referred to as a source apparatus) having a function of transmitting information (hereinafter also referred to as display information) to be displayed during surgery. Moreover, the displays 5103A to 5103D may be an apparatus (hereinafter also referred to as a destination apparatus) to which the display information is output. Moreover, the recorder 5105 may be an apparatus that corresponds to both the source apparatus and the destination apparatus. The AV controller 5107 has a function of controlling the operation of the source apparatus and the destination apparatus to acquire display information from the source apparatus and transmitting the display information to the destination apparatus to display or record the display information. Here, the display information includes various images acquired during surgery and various pieces of information related to surgery (for example, physical information of a patient, past examination results, information on a surgery method, and the like).

Specifically, information on images of a surgical area in the body cavity of a patient acquired by the endoscope may be transmitted from the apparatus group 5101 to the AV controller 5107 as the display information. Moreover, information on images of the hands of an operator acquired by the ceiling camera 5187 may be transmitted from the ceiling camera 5187 as the display information. Moreover, information on images indicating the view of the entire operating room acquired by the room camera 5189 may be transmitted from the room camera 5189 as the display information. Here, when another apparatus having an imaging function is present in the operating room system 5100, the AV controller 5107 may acquire the information on images acquired by the other apparatus from the other apparatus.

Alternatively, for example, information on these images acquired in the past is recorded in the recorder 5105 by the AV controller 5107. The AV controller 5107 can acquire the information on images acquired in the past from the recorder 5105 as the display information. Here, various pieces of invitation notification related to operation may be recorded in advance in the recorder 5105.

The AV controller 5107 displays the acquired display information (that is, images captured during surgery and various pieces of information related to surgery) on at least one of the displays 5103A to 5103D which are destination apparatuses. In the illustrated example, the display 5103A is a display provided in a state of being suspended from the ceiling of the operating room, the display 5103B is a display provided on a wall of the operating room, the display 5103C is a display provided on a table in the operating room, and the display 5103D is a mobile apparatus (for example, a tablet personal computer (PC)) having a display function.

Moreover, although not illustrated in FIG. 19, an external apparatus of the operating room may be included in the operating room system 5100. The external apparatus of the operating room system includes, for example, a server connected to a network constructed inside and outside a hospital, PCs used by medical staffs, a projector provided in a meeting room of a hospital, and the like. When such an external apparatus is outside a hospital, the AV controller 5107 may display display information on a display of another hospital via a TV conference system or the like in order to conduct a telemedical diagnosis.

The operating room controller 5109 controls processings other than processings related to image display of the non-medical apparatuses in an integrated manner. For example, the operating room controller 5109 controls driving of the patient bed 5183, the ceiling camera 5187, the room camera 5189, and the illumination 5191.

The central operation panel 5111 is provided in the operating room system 5100, and a user can output an instruction related to image display to the AV controller 5107 via the central operation panel 5111 and output an instruction related to operation of non-medical apparatuses to the operating room controller 5109. The central operation panel 5111 is formed in such a way that a touch panel is formed on a display surface of a display.

Figure 20:
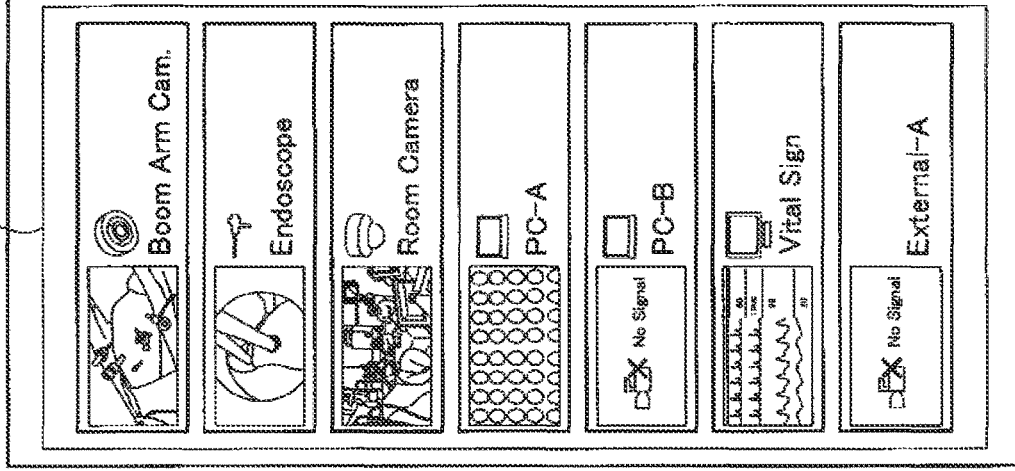
FIG. 20 is a diagram illustrating a display example of an operation screen on a central operation panel.

FIG. 20 is a diagram illustrating a display example of an operation screen of the central operation panel 5111.

FIG. 20 illustrates an operation screen when two displays as destination apparatuses are provided in the operating room system 5100 as an example. Referring to FIG. 20, a source selection region 5195, a preview region 5197, and a control region 5201 are provided in an operation screen 5193.

Source apparatuses provided in the operating room system 5100 and a thumbnail screen indicating the display information of the source apparatuses are displayed in the source selection region 5195 in association. A user can select display information to be displayed on a display from either one of source apparatuses displayed in the source selection region 5195.

A preview of a screen displayed on two displays (Monitor 1, Monitor 2) which are destination apparatuses is displayed in the preview region 5197. In the illustrated example, four images are displayed in one display in a PinP form. The four images correspond to pieces of display information transmitted from the selected source apparatus in the source selection region 5195. Among the four images, one image is displayed relatively large as a main image, and the remaining images are displayed relatively small as sub-images. A user can replace the main image and the sub-images with each other by selecting a region in which four images are displayed appropriately. Moreover, a status display region 5199 is provided in a lower part of a region in which four images are displayed, and the status (for example, the time elapsed of operation, physical information of a patient, and the like) related to operation is displayed appropriately in the region.

A source operating region 5203 in which graphical user interface (GUI) components for operating the source apparatus are displayed and a destination operating region 5205 in which GUI components for operating the destination apparatus are displayed are provided in the control region 5201. In the illustrated example, GUI components for performing various operations (panning, tilting, and zooming) on a camera of the source apparatus having an imaging function are provided in the source operating region 5203. A user can operate the operation of a camera of the source apparatus by selecting these GUI components appropriately. Moreover, although not illustrated in the drawing, when the source apparatus selected in the source selection region 5195 is a recorder (that is, an image recorded in the past in the recorder is displayed in the preview region 5197), GUI components for performing operations such as playback of the image, stopping of playback, rewinding, and fast-forwarding are provided in the source operating region 5203.

Moreover, GUI components for performing various operations (swapping, flipping, color adjustment, contrast adjustment, and switching between 2D and 3D display) with respect to the display on a display which is a destination apparatus are provided in the destination operating region 5205. A user can operate the display on the display by selecting these GUI components appropriately.

Here, the operation screen displayed on the central operation panel 5111 is not limited to the illustrated example, and a user may be able to input operations for respective apparatuses which are controlled by the AV controller 5107 and the operating room controller 5109, provided in the operating room system 5100 via the central operation panel 5111.

Figure 21:
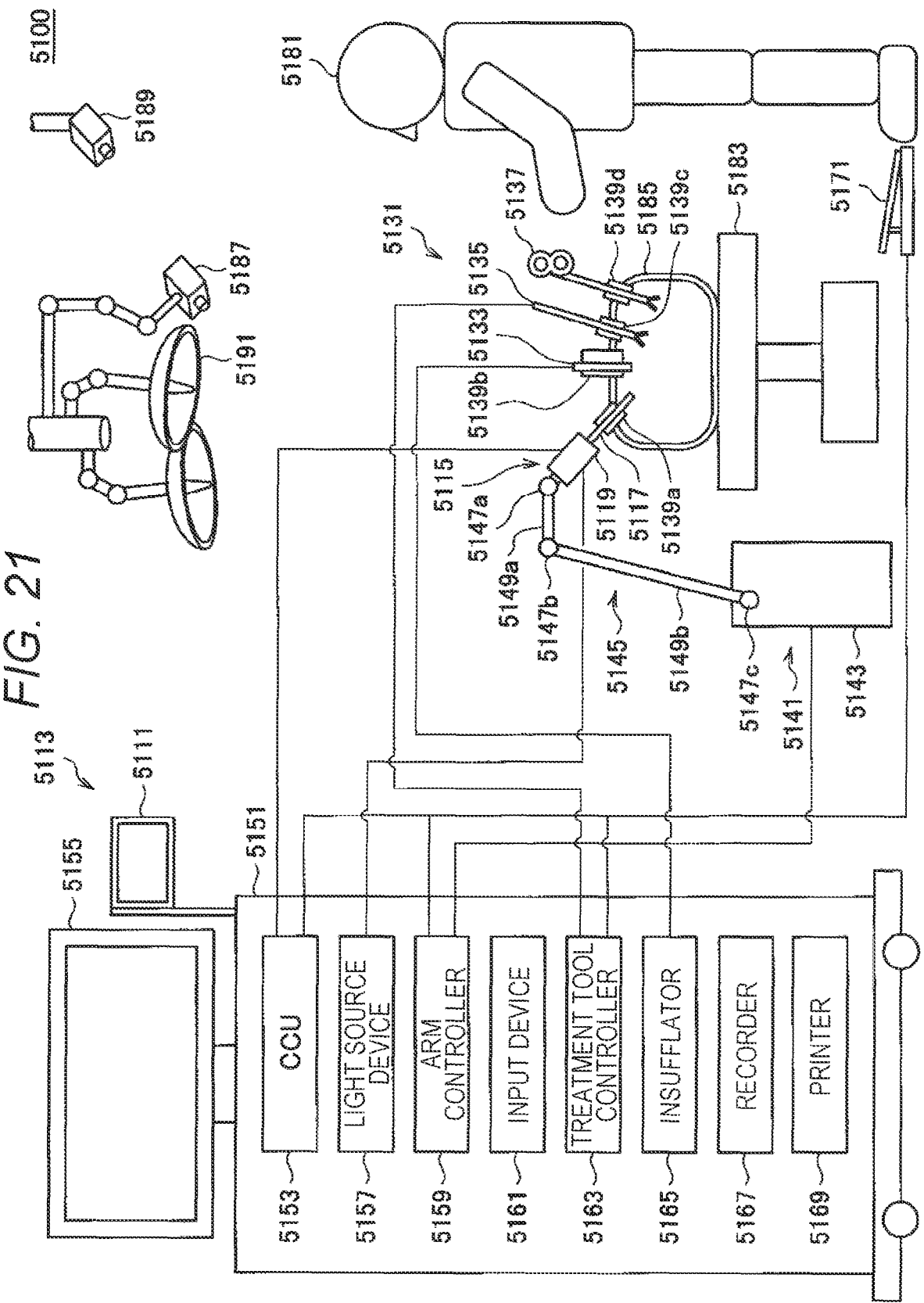
FIG. 21 is a diagram illustrating an example of how an operation to which an operating room system is applied is performed.

FIG. 21 is a diagram illustrating an example of how an operation to which the operating room system described above is applied. The ceiling camera 5187 and the room camera 5189 are provided on the ceiling of an operating room and can image the view of the entire operating room and the hands of an operator (a physician) 5181 who performs treatments on an affected area of a patient 5185 on the patient bed 5183. The ceiling camera 5187 and the room camera 5189 have a magnification adjustment function, a focal distance adjustment function, a photographing direction adjustment function, and the like. The illumination 5191 is provided on the ceiling of an operating room and illuminates at least the hands of the operator 5181. The illumination 5191 can adjust the amount of emission light, the wavelength (color) of emission light, an emission direction of light, and the like appropriately.

As illustrated in FIG. 19, the endoscopic surgery system 5113, the patient bed 5183, the ceiling camera 5187, the room camera 5189, and the illumination 5191 are connected via the AV controller 5107 and the operating room controller 5109 (not illustrated in FIG. 21) so as to cooperate with each other. The central operation panel 5111 is provided in the operating room, and as described above, a user can appropriately operate these apparatuses present in the operating room via the central operation panel 5111.

Hereinafter, a configuration of the endoscopic surgery system 5113 will be described in detail. As illustrated in the drawing, the endoscopic surgery system 5113 includes an endoscope 5115, other surgical instruments 5131, a supporting arm apparatus 5141 that supports the endoscope 5115, and a cart 5151 on which various apparatuses for endoscopic surgery are mounted.

In endoscopic surgery, a plurality of tubular perforating tools called trocars 5139a to 5139d perforates a plurality of holes into an abdominal wall instead of incising and opening the abdominal wall. Moreover, a barrel 5117 of the endoscope 5115 and other surgical instruments 5131 are inserted into the body cavity of the patient 5185 from the trocars 5139a to 5139d. In the illustrated example, an insufflation tube 5133, an energy treatment tool 5135, and forceps 5137 are inserted into the body cavity of the patient 5185 as the other surgical instruments 5131. Moreover, the energy treatment tool 5135 is a treatment tool that performs incision and peeling of tissues, sealing of blood vessels, or the like by supplying high-frequency current or ultrasound vibration.

However, the illustrated surgical instruments 5131 are examples only, and various surgical instruments generally used in endoscopic surgery such as tweezers and a retractor may be used as the surgical instruments 5131.

The images of the surgical area in the body cavity of the patient 5185 acquired by the endoscope 5115 are displayed on a display 5155. The operator 5181 performs treatments of incising an affected area or the like, for example, using the energy treatment tool 5135 and the forceps 5137 while watching the real-time images of the surgical area displayed on the display 5155. Although not illustrated in the drawing, the insufflation tube 5133, the energy treatment tool 5135, and the forceps 5137 are supported by the operator 5181 or an assistant or the like during surgery.

(Supporting Arm Apparatus)

The supporting arm apparatus 5141 includes an arm 5145 extending from a base 5143. In the illustrated example, the arm 5145 includes joints 5147a, 5147b, and 5147c and links 5149a and 5149b and are driven by the control of an arm controller 5159. The endoscope 5115 is supported by the arm 5145 and the position and the attitude thereof are controlled. In this way, the position of the endoscope 5115 is fixed stably.

(Endoscope)

The endoscope 5115 includes the barrel 5117 of which a predetermined length of region from a distal end thereof is inserted into the body cavity of the patient 5185 and a camera head 5119 connected to a base end of the barrel 5117. In the illustrated example, although the endoscope 5115 formed as a so-called rigid mirror having a rigid barrel 5117 is illustrated, the endoscope 5115 may be configured as a so-called soft mirror having a soft barrel 5117.

An opening having an objective lens fitted thereto is formed in a distal end of the barrel 5117. A light source device 5157 is connected to the endoscope 5115, and light generated by the light source device 5157 is guided to the distal end of the barrel by a light guide extended into the inside of the barrel 5117 and is radiated toward an observation target in the body cavity of the patient 5185 via the objective lens. Here, the endoscope 5115 may be a direct-view mirror and may be an oblique-view mirror or a side-view mirror.

An optical system and an imaging element are provided inside the camera head 5119, and reflection light (observation light) from the observation target is focused on the imaging element by the optical system. The observation light is photoelectrically converted by the imaging element and an electrical signal (that is, an image signal corresponding to an observation image) corresponding to the observation light is generated. The image signal is transmitted to a camera control unit (CCU) 5153 as raw data. Here, the camera head 5119 has a function of adjusting a magnification and a focal distance by driving the optical system thereof appropriately.

Here, a plurality of imaging elements may be provided in the camera head 5119 in order to cope with stereoscopic view (3D display) or the like, for example. In this case, a plurality of relay optical systems is provided inside the barrel 5117 in order to guide observation light of the plurality of imaging elements.

(Various Apparatuses Mounted on Cart)

The CCU 5153 is configured as a central processing unit (CPU), a graphics processing unit (GPU), and the like and controls the operation of the endoscope 5115 and the display 5155 in an integrated manner. Specifically, the CCU 5153 performs various image processings (for example, developing processing (demosaic processing) or the like) for displaying an image based on the image signal received from the camera head 5119. The CCU 5153 provides the processed image signal to the display 5155. Moreover, the AV controller 5107 illustrated in FIG. 19 is connected to the CCU 5153. The CCU 5153 also provides the processed image signal to the AV controller 5107. Moreover, the CCU 5153 transmits a control signal to the camera head 5119 to control the driving thereof. The control signal includes information regarding imaging conditions such as a magnification and a focal distance. The information regarding the imaging conditions may be input via an input device 5161 and may be input via the central operation panel 5111 described above.

The display 5155 displays an image based on the image signal processed by the CCU 5153 by the control from the CCU 5153. When the endoscope 5115 copes with high-resolution imaging of 4K (3840 (H)×2160 (V) pixels), 8K (7680 (H)×4320 (V) pixels), or the like, for example, and/or copes with 3D display, a display capable of performing high-resolution display and/or a display capable of performing 3D display is used as the display 5155. When the endoscope copes with high-resolution imaging of 4K, 8K, or the like, a higher level of immersion is acquired by using a display of the size of 55 inches or larger as the display 5155. Moreover, a plurality of displays 5155 having different resources and sizes may be provided depending on use.

The light source device 5157 includes a light source such as a light emitting diode (LED), for example, and supplies radiation light when imaging a surgical area to the endoscope 5115.

The arm controller 5159 is configured as a processor such as a CPU, for example, and operates according to a predetermined program to control the driving of the arm 5145 of the supporting arm apparatus 5141 according to a predetermined control method.

The input device 5161 is an input interface for the endoscopic surgery system 5113. A user can input various pieces of information and instructions to the endoscopic surgery system 5113 via the input device 5161. For example, a user inputs various pieces of information related to surgery such as the physical information of a patient and information on a surgery method via the input device 5161. Moreover, for example, a user inputs an instruction or the like of driving the arm 5145, an instruction of changing the imaging conditions (the type of radiation light, a magnification, a focal distance, and the like) of the endoscope 5115, and an instruction of driving the energy treatment tool 5135 via the input device 5161.

The type of the input device 5161 is not limited, and the input device 5161 may be various known input devices. For example, a mouse, a keyboard, a touch panel, a switch, a foot switch 5171, and/or a lever or the like may be used as the input device 5161. When a touch panel is used as the input device 5161, the touch panel may be provided on a display surface of the display 5155.

Alternatively, the input device 5161 is a device worn on a user such as a glasses-type wearable device or a head mounted display (HMD), for example, and inputs various pieces of information depending on the gesture and the line of sight of the user detected by these devices. Moreover, the input device 5161 includes a camera capable of detecting the motion of a user and inputs various pieces of information depending on the gesture and the line of sight of the user detected from a video captured by the camera. Furthermore, the input device 5161 includes a microphone capable of collecting the sound of a user and inputs various pieces of information via voice using the microphone. In this manner, since the input device 5161 is configured to be able to input various pieces of information in a contactless manner, a user (for example, the operator 5181) belonging to a clean region particularly can operate an apparatus belonging to an unclean region in a contactless manner. Moreover, since a user can operate apparatuses without separating hands from tools that the user is holding, the user's convenience is improved.

A treatment tool controller 5163 controls the driving of the energy treatment tool 5135 for cauterizing and incising tissues, sealing blood vessels, or the like. An insufflator 5165 supplies gas into the body cavity via the insufflation tube 5133 in order to inflate the body cavity of the patient 5185 for the purpose of securing the view of the endoscope 5115 and securing the operation space of the operator. A recorder 5167 is a device capable of recording various pieces of information related to surgery. A printer 5169 is a device capable of printing various pieces of information related to surgery in various forms such as text, an image, or a graph.

Hereinafter, a configuration particularly characteristic in the endoscopic surgery system 5113 will be described in further detail.

(Supporting Arm Apparatus)

The supporting arm apparatus 5141 includes the base 5143 which is a base and the arm 5145 extending from the base 5143. In the illustrated example, the arm 5145 includes a plurality of joints 5147a, 5147b, and 5147c and a plurality of links 5149a and 5149b connected by the joint 5147b. However, for the simplicity sake, the configuration of the arm 5145 is illustrated in a simplified manner in FIG. 21. Actually, the shape, the number and the arrangement of the joints 5147a to 5147c and the links 5149a and 5149b, the directions of the rotation axes of the joints 5147a to 5147c, and the like are set appropriately so that the arm 5145 has a desired degree of freedom. For example, the arm 5145 may preferably have a degree of freedom of 6 or higher. In this way, since the endoscope 5115 can be moved freely within a movable range of the arm 5145, the barrel 5117 of the endoscope 5115 can be inserted into the body cavity of the patient 5185 from a desired direction.

An actuator is provided in the joints 5147a to 5147c, and the joints 5147a to 5147c are configured to be able to rotate about a predetermined rotation axis by the driving of the actuator. When the driving of the actuator is controlled by the arm controller 5159, the rotation angles of the joints 5147a to 5147c are controlled and the driving of the arm 5145 is controlled. In this way, the position and the attitude of the endoscope 5115 can be controlled. In this case, the arm controller 5159 can control driving of the arm 5145 by various known control methods such as force control or position control.

For example, the operator 5181 may input operations appropriately via the input device 5161 (including the foot switch 5171), whereby driving of the arm 5145 may be controlled appropriately by the arm controller 5159 in response to the operations and the position and the attitude of the endoscope 5115 may be controlled. With this control, after the endoscope 5115 at the distal end of the arm 5145 is moved from an arbitrary position to an arbitrary position, the endoscope 5115 can be supported fixedly at the position after the movement. Here, it is to be noted that the arm 5145 may be operated in a so-called master-slave fashion. In this case, the arm 5145 may be remotely controlled by the user via the input device 5161 provided at a place remote from the operating room.

Moreover, when force control is applied, the arm controller 5159 may perform so-called power-assisted control of driving the actuators of the joints 5147*a* to 5147*c* so that the arm 5145 receives external force from the user and moves smoothly following the external force. In this way, the user can move the arm 5145 with comparatively weak force when the user moves the arm 5145 while directly touching the arm 5145. Therefore, it is possible to move the endoscope 5115 more intuitively by a simpler operation, and the user's convenience can be improved.

Here, generally, in endoscopic surgery, the endoscope 5115 is supported by a medical doctor called a scopist. In contrast, by using the supporting arm apparatus 5141, since the position of the endoscope 5115 can be fixed more reliably without hands, an image of an affected surgical area can be acquired stably and surgery can be performed smoothly.

Here, it is to be noted that the arm controller 5159 may not necessarily be provided on the cart 5151. Moreover, the arm controller 5159 may not necessarily be a single apparatus. For example, the arm controller 5159 may be provided in each of the joints 5147*a* to 5147*c* of the arm 5145 of the supporting arm apparatus 5141, and a plurality of arm controllers 5159 may cooperate with each other whereby the driving of the arm 5145 may be controlled.

(Light Source Device)

The light source device 5157 supplies radiation light when imaging a surgical area to the endoscope 5115. The light source device 5157 is configured as a white light source which includes, for example, an LED, a laser light source, or a combination thereof. In this case, when a white light source includes a combination of red, green, and blue (RGB) laser light sources, since the output intensity and the output timing for each color (each wavelength) can be controlled with high accuracy, the white balance of a captured image can be adjusted by the light source device 5157. Moreover, in this case, when laser beams from the RGB laser light sources are radiated time-divisionally to an observation target and driving of the imaging elements of the camera head 5119 is controlled in synchronism with the radiation timings, images corresponding to the colors R, G and B can be captured time-divisionally. According to this method, a color image can be acquired even when a color filter is not provided for the imaging element.

Moreover, driving of the light source device 5157 may be controlled such that the intensity of light to be outputted is changed for each predetermined time. By controlling driving of the imaging element of the camera head 5119 in synchronism with the timing of the change of the intensity of light to acquire images time-divisionally and synthesizing the images, an image of a high dynamic range free from underexposed blocked up shadows and overexposed highlights can be created.

Moreover, the light source device 5157 may be configured to supply light of a predetermined wavelength band compatible with special light observation. In special light observation, for example, by utilizing the wavelength dependency of absorption of light of a body tissue to radiate light of a narrower band in comparison with radiation light during ordinary observation (namely, white light), narrow band light observation (narrow band imaging) of imaging a predetermined tissue such as a blood vessel of a superficial portion of the mucous membrane in a high contrast is performed. Alternatively, in special light observation, fluorescent observation for obtaining an image from fluorescent light generated by radiation of excitation light may also be performed. In fluorescent observation, it is possible to perform observation of fluorescent light from a body tissue by radiating excitation light on the body tissue (autofluorescence observation) or, for example, to obtain a fluorescent light image by locally injecting a reagent such as indocyanine green (ICG) into a body tissue and radiating excitation light corresponding to a fluorescent light wavelength of the reagent to the body tissue. The light source device 5157 is configured to be able to supply a narrow-band light and/or excitation light suitable for such special light observation.

(Camera Head and CCU)

Figure 22:
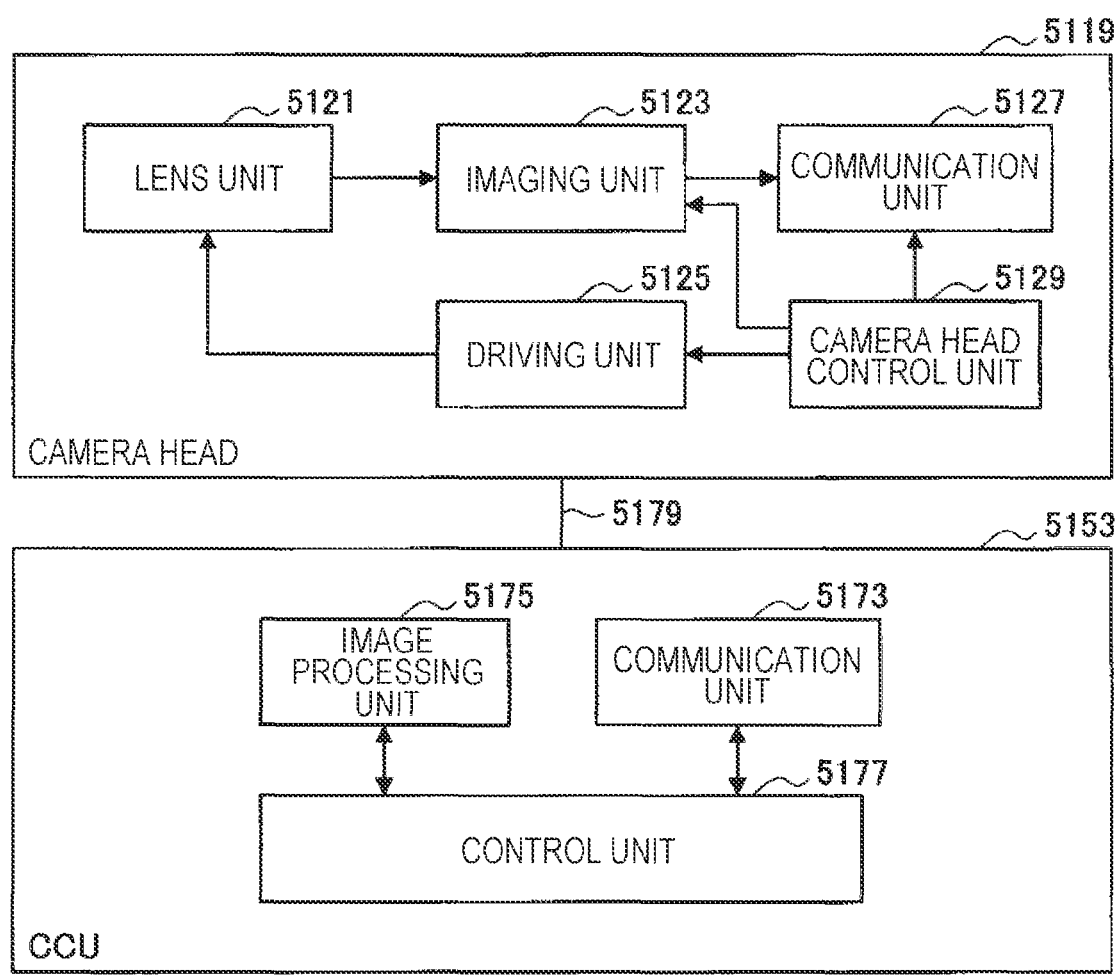
FIG. 22 is a block diagram illustrating an example of a functional configuration of a CCU and a camera head illustrated in FIG. 21.

Functions of the CCU 5153 and the camera head 5119 of the endoscope 5115 will be described in more detail with reference to FIG. 22. FIG. 22 is a block diagram illustrating an example of a functional configuration of the camera head 5119 and the CCU 5153 illustrated in FIG. 21.

Referring to FIG. 22, the camera head 5119 has, as functions thereof, a lens unit 5121, an imaging unit 5123, a driving unit 5125, a communication unit 5127 and a camera head control unit 5129. Moreover, the CCU 5153 has, as functions thereof, a communication unit 5173, an image processing unit 5175 and a control unit 5177. The camera head 5119 and the CCU 5153 are connected to be bidirectionally communicable with each other by a transmission cable 5179.

First, a functional configuration of the camera head 5119 will be described. The lens unit 5121 is an optical system provided at a connecting location of the camera head 5119 to the barrel 5117. Observation light taken in from a distal end of the barrel 5117 is introduced into the camera head 5119 and enters the lens unit 5121. The lens unit 5121 includes a combination of a plurality of lenses including a zoom lens and a focusing lens. The lens unit 5121 has optical properties adjusted such that the observation light is focused on a light receiving surface of the imaging element of the imaging unit 5123. Moreover, the zoom lens and the focusing lens are configured such that the positions thereof on their optical axis are movable for adjustment of the magnification and the focal point of a captured image.

The imaging unit 5123 is configured as an imaging element and disposed at a rear stage to the lens unit 5121. Observation light having passed through the lens unit 5121 is focused on the light receiving surface of the imaging element, and an image signal corresponding to the observation image is generated by photoelectric conversion. The image signal generated by the imaging unit 5123 is provided to the communication unit 5127.

As the imaging element which is included in the imaging unit 5123, an image sensor, for example, of the complementary metal oxide semiconductor (CMOS) type, which has a Bayer array and is capable of acquiring color images is used. Here, it is to be noted that, as the imaging element, an imaging element which is capable of, for example, imaging an image of a high resolution of 4K or higher may be used. When an image of a surgical area is acquired in a high resolution, the operator 5181 can understand the state of the surgical area in more detail and can proceed with the surgery more smoothly.

Moreover, the imaging element which is included in the imaging unit 5123 has a pair of imaging elements for acquiring image signals for the right eye and the left eye compatible with 3D display. When 3D display is applied, the operator 5181 can understand the depth of a biological tissue in the surgical area with a higher degree of accuracy. Here, it is to be noted that, when the imaging unit 5123 is configured as a multi-plate type imaging unit, a plurality of systems of lens units 5121 are so as to correspond to the respective imaging elements.

Moreover, the imaging unit 5123 may not necessarily be provided on the camera head 5119. For example, the imaging unit 5123 may be provided inside the barrel 5117 immediately behind the objective lens.

The driving unit 5125 is configured as an actuator and moves the zoom lens and the focusing lens of the lens unit 5121 by a predetermined distance along the optical axis by the control of the camera head control unit 5129. In this way, the magnification and the focal point of a captured image by the imaging unit 5123 can be adjusted suitably.

The communication unit 5127 is configured as a communication apparatus for transmitting and receiving various pieces of information to and from the CCU 5153. The communication unit 5127 transmits an image signal acquired from the imaging unit 5123 as raw data to the CCU 5153 via the transmission cable 5179. In this case, in order to display a captured image of a surgical area with low latency, the image signal is preferably transmitted by optical communication. This is because, since, during surgery, the operator 5181 performs surgery while observing the state of an affected area via a captured image, in order to achieve surgery with a higher degree of safety and reliability, it is necessary to display a moving image of the surgical area on the real time basis as much as possible. When optical communication is applied, a photoelectric conversion module for converting an electrical signal into an optical signal is provided in the communication unit 5127. After the image signal is converted into an optical signal by the photoelectric conversion module, the image signal is transmitted to the CCU 5153 via the transmission cable 5179.

Moreover, the communication unit 5127 receives a control signal for controlling driving of the camera head 5119 from the CCU 5153. The control signal includes information related to imaging conditions such as, for example, information that designates a frame rate of a captured image, information that designates an exposure value during imaging, and/or information that designates a magnification and a focal point of a captured image. The communication unit 5127 provides the received control signal to the camera head control unit 5129. Here, it is to be noted that the control signal from the CCU 5153 may be also transmitted by optical communication. In this case, a photoelectric conversion module for converting an optical signal into an electrical signal is provided in the communication unit 5127. After the control signal is converted into an electrical signal by the photoelectric conversion module, the electrical signal is provided to the camera head control unit 5129.

Here, it is to be noted that the imaging conditions such as a frame rate, an exposure value, a magnification, or a focal point are set automatically by the control unit 5177 of the CCU 5153 on the basis of an acquired image signal. In other words, an auto exposure (AE) function, an auto focus (AF) function, and an auto white balance (AWB) function are incorporated in the endoscope 5115.

The camera head control unit 5129 controls driving of the camera head 5119 on the basis of a control signal from the CCU 5153 received via the communication unit 5127. For example, the camera head control unit 5129 controls driving of the imaging element of the imaging unit 5123 on the basis of information that designates a frame rate of a captured image and/or information that designates an exposure value during imaging. Moreover, for example, the camera head control unit 5129 controls the driving unit 5125 to appropriately move the zoom lens and the focus lens of the lens unit 5121 on the basis of information that designates a magnification and a focal point of a captured image. The camera head control unit 5129 may include a function for storing information for identifying the barrel 5117 and/or the camera head 5119.

Here, it is to be noted that, by arranging the components such as the lens unit 5121 and the imaging unit 5123 in a sealed structure having high air-tightness and high waterproofness, the camera head 5119 can be provided with resistance to autoclave sterilization processing.

Next, a functional configuration of the CCU 5153 will be described. The communication unit 5173 is configured as a communication apparatus for transmitting and receiving various pieces of information to and from the camera head 5119. The communication unit 5173 receives an image signal transmitted from the camera head 5119 via the transmission cable 5179. In this case, the image signal may be transmitted preferably by optical communication as described above. In this case, for optical communication, the communication unit 5173 includes a photoelectric conversion module for converting an optical signal into an electrical signal. The communication unit 5173 provides the image signal converted into an electrical signal to the image processing unit 5175.

Moreover, the communication unit 5173 transmits a control signal for controlling driving of the camera head 5119 to the camera head 5119. The control signal may be transmitted by optical communication.

The image processing unit 5175 performs various image processings for an image signal in the form of raw data transmitted thereto from the camera head 5119. Image processings include various known signal processings such as, for example, developing processing, image quality improving processing (bandwidth enhancement processing, super-resolution processing, noise reduction (NR) processing and/or image stabilization processing) and/or enlargement processing (electronic zooming processing), or the like. Moreover, the image processing unit 5175 performs detection processing for an image signal for performing AE, AF and AWB.

The image processing unit 5175 is configured as a processor such as a CPU or a GPU, and when the processor operates according to a predetermined program, image processings and detection processing described above can be performed. Here, it is to be noted that, when the image processing unit 5175 is configured as a plurality of GPUs, the image processing unit 5175 appropriately divides information related to an image signal such that image processings are performed in parallel by the plurality of GPUs.

The control unit 5177 performs various kinds of control related to imaging of a surgical area by the endoscope 5115 and display of the captured image. For example, the control unit 5177 generates a control signal for controlling driving of the camera head 5119. In this case, when imaging conditions are inputted by the user, the control unit 5177 generates a control signal on the basis of the user's input. Alternatively, when the endoscope 5115 has an AE function, an AF function and an AWB function incorporated therein, the control unit 5177 appropriately calculates an optimum exposure value, focal distance and white balance according to the results of detection processing by the image processing unit 5175 and generates a control signal.

Moreover, the control unit 5177 controls the display 5155 to display an image of a surgical area on the basis of an image signal for which image processings have been performed by the image processing unit 5175. In this case, the control unit 5177 recognizes various objects in the surgical area image using various image recognition technologies. For example, the control unit 5177 can recognize a surgical tool such as forceps, a particular living body region, bleeding, mist when the energy treatment tool 5135 is used and the like by detecting the shape, color and the like of edges of the objects included in the surgical area image. When the control unit 5177 causes the display 5155 to display a surgical area image, the control unit 5177 displays various pieces of surgery supporting information so as to be superimposed on the image of the surgical area using the recognition results. When surgery supporting information is displayed in a superimposed manner and is presented to the operator 5181, the operator 5181 can proceed with the surgery with more safety and reliability.

The transmission cable 5179 which connects the camera head 5119 and the CCU 5153 to each other is an electrical signal cable compatible with communication of electrical signals, an optical fiber compatible with optical communication or a composite cable thereof.

Here, in the illustrated example, although communication is performed by wired communication using the transmission cable 5179, the communication between the camera head 5119 and the CCU 5153 may be performed by wireless communication. When the communication between the camera head 5119 and the CCU 5153 is performed by wireless communication, it is not necessary to lay the transmission cable 5179 in the operating room. Therefore, it is possible to eliminate a situation in which movement of medical staff in the operating room is disturbed by the transmission cable 5179.

Hereinabove, an example of the operating room system 5100 to which the technology according to an embodiment of the present disclosure can be applied has been described above. Here, it is to be noted that, although a case in which the medical system to which the operating room system 5100 is applied is the endoscopic surgery system 5113 has been described as an example, the configuration of the operating room system 5100 is not limited to that of the example described above. For example, the operating room system 5100 may be applied to a soft endoscopic system for inspection or a microscopic surgery system in place of the endoscopic surgery system 5113.

The technology according to the present disclosure can be applied to the imaging unit 5123 of the camera head 5119. More specifically, the imaging unit 5123 may include a splitter that splits incident light from the lens unit 5121 into pieces of light of two or more wavelength bands and two or more detectors that detect the pieces of light of two or more wavelength bands and output signals from which wavelengths can be extracted tunably by post-processing. In this way, the operating room system 5100 can extract wavelengths tunably while maintaining high wavelength reproducibility and a high S/N ratio.

4.3. Application Example to Vehicle Control System

Next, an example of a case in which the technology according to the present disclosure is applied to a vehicle control system for any one of mobile objects such as automobiles, electric vehicles, hybrid electric vehicles, motorcycles, bicycles, personal mobilities, airplanes, drones, ships, robots, construction machines, and agricultural machines (tractors).

Figure 23:
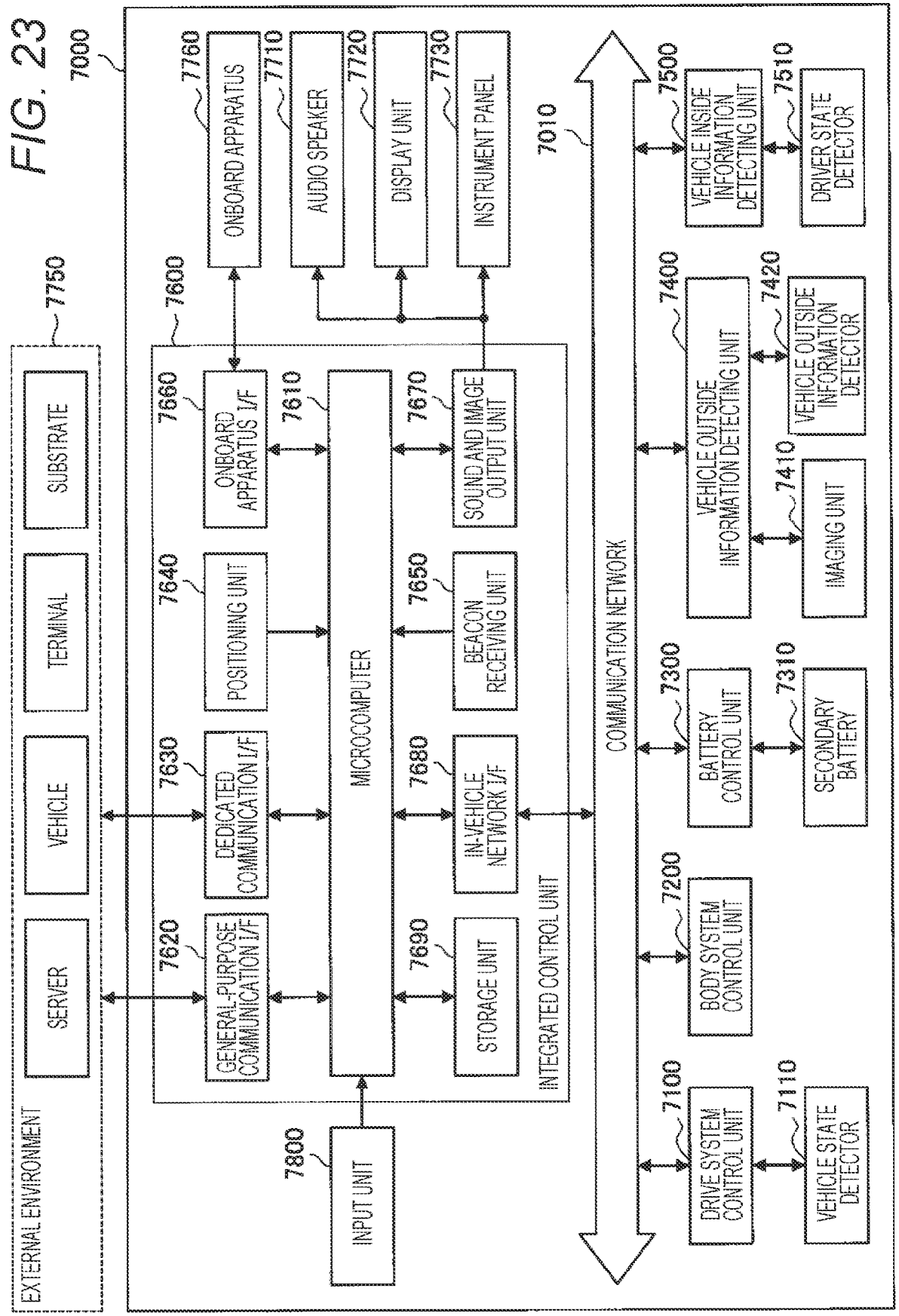
FIG. 23 is a block diagram illustrating an example of a schematic configuration of a vehicle control system.

FIG. 23 is a block diagram illustrating a schematic configuration example of a vehicle control system 7000 that is an example of a mobile object control system to which the technology according to the present disclosure can be applied. The vehicle control system 7000 includes a plurality of electronic control units connected via a communication network 7010. In the example illustrated in FIG. 23, the vehicle control system 7000 includes a drive system control unit 7100, a body system control unit 7200, a battery control unit 7300, a vehicle outside information detecting unit 7400, a vehicle inside information detecting unit 7500, and an integrated control unit 7600. The communication network 7010, which connects these control units, may be an in-vehicle communication network compliant with an arbitrary standard such as a controller area network (CAN), a local interconnect network (LIN), a local area network (LAN), or FlexRay (registered trademark).

Each control unit includes a microcomputer that performs operation processing according to various programs, a storage unit that stores the programs, parameters used for the variety of operations, or the like executed by the microcomputer, and a driving circuit that drives apparatuses subjected to various types of control. Each control unit includes a network I/F used to communicate with the other control units via the communication network 7010, and a communication I/F used to communicate with apparatuses, sensors, or the like outside and inside the vehicle via wired communication or wireless communication. FIG. 23 illustrates a microcomputer 7610, a general-purpose communication I/F 7620, a dedicated communication I/F 7630, a positioning unit 7640, a beacon receiving unit 7650, an onboard apparatus I/F 7660, a sound and image output unit 7670, an in-vehicle network I/F 7680, and a storage unit 7690 as functional components of the integrated control unit 7600. Each of the other control units similarly includes a microcomputer, a communication I/F, a storage unit, and the like.

The drive system control unit 7100 controls the operation of apparatus related to the drive system of the vehicle according to various programs. For example, the drive system control unit 7100 functions as a control apparatus for a driving force generating apparatus such as an internal combustion engine or a driving motor that generates the driving force of the vehicle, a driving force transferring mechanism that transfers the driving force to wheels, a steering mechanism that adjusts the steering angle of the vehicle, a braking apparatus that generates the braking force of the vehicle, and the like. The drive system control unit 7100 may have the function of a control apparatus for an antilock brake system (ABS) or an electronic stability control (ESC).

The drive system control unit 7100 is connected to a vehicle state detector 7110. The vehicle state detector 7110 includes, for example, at least one of sensors such as a gyro sensor that detects the angular velocity of the axial rotating motion of the vehicle body, an acceleration sensor that detects the acceleration of the vehicle, or a sensor that detects the operation amount of the accelerator pedal, the operation amount of the brake pedal, the steering wheel angle of the steering wheel, the engine speed, the wheel rotation speed, or the like. The drive system control unit 7100 uses a signal input from the vehicle state detector 7110 to perform operation processing, and controls the internal combustion engine, the driving motors, the electric power steering apparatus, the braking apparatus, or the like.

The body system control unit 7200 controls the operations of various apparatuses attached to the vehicle body according to various programs. For example, the body system control unit 7200 functions as a control apparatus for a keyless entry system, a smart key system, a power window apparatus, or various lights such as a headlight, a backup light, a brake light, a blinker, or a fog lamp. In this case, the body system control unit 7200 can receive radio waves transmitted from a portable apparatus that serves instead of the key or signals of various switches. The body system control unit 7200 receives these radio waves or signals, and controls the vehicle door lock apparatus, the power window apparatus, the lights, or the like.

The battery control unit 7300 controls a secondary battery 7310 which is a power supply source of a driving motor according to various programs. For example, the battery control unit 7300 receives information such as the battery temperature, the battery output voltage, or the remaining battery capacity from a battery apparatus including the secondary battery 7310. The battery control unit 7300 uses these signals to perform operation processing, and performs temperature adjusting control on the secondary battery 7310 or controls a cooling apparatus or the like included in the battery apparatus.

The vehicle outside information detecting unit 7400 detects information regarding the outside of the vehicle including the vehicle control system 7000. For example, the vehicle outside information detecting unit 7400 is connected to at least one of an imaging unit 7410 or a vehicle outside information detector 7420. The imaging unit 7410 includes at least one of a time of flight (ToF) camera, a stereo camera, a monocular camera, an infrared camera, or other cameras. The vehicle outside information detector 7420 includes, for example, at least one of an environment sensor that detects the current weather, or a surrounding information detecting sensor that detects another vehicle, an obstacle, a pedestrian, or the like around the vehicle including the vehicle control system 7000.

The environment sensor may be, for example, at least one of a raindrop sensor that detects rainy weather, a fog sensor that detects a fog, a sunshine sensor that detects the degree of sunshine, or a snow sensor that detects a snowfall. The surrounding information detecting sensor may be at least one of an ultrasonic sensor, a radar apparatus, or a light detection and ranging/laser imaging detection and ranging (LIDAR) apparatus. The imaging unit 7410 and the vehicle outside information detector 7420 may be installed as independent sensors or apparatuses, or as an apparatus into which sensors and apparatuses are integrated.

Figure 24:
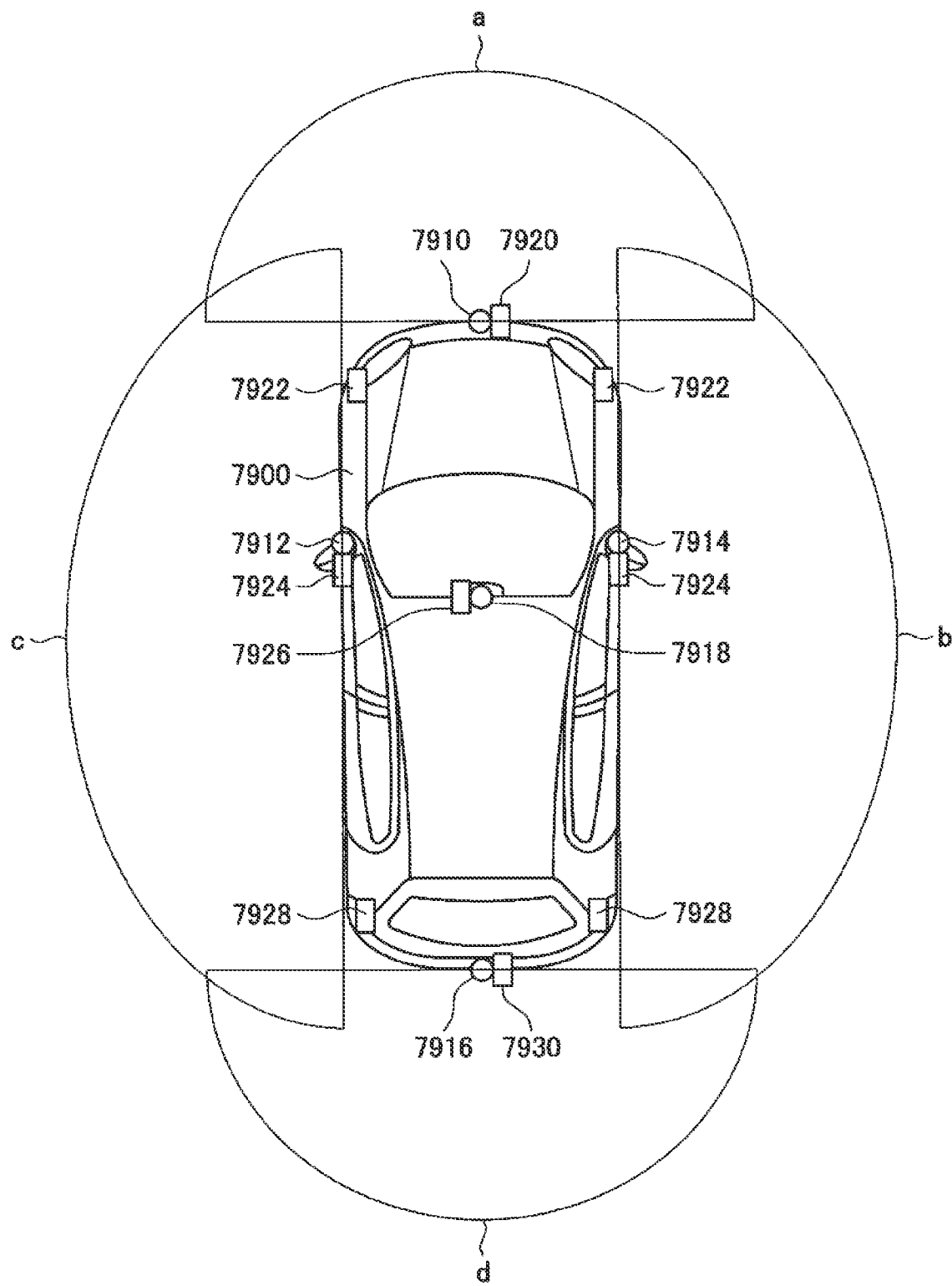
FIG. 24 is an explanatory diagram illustrating an example of the installed positions of a vehicle outside information detector and an imaging unit.

Here, FIG. 24 illustrates an example of the installation positions of the imaging unit 7410 and the vehicle outside information detector 7420. Imaging units 7910, 7912, 7914, 7916, and 7918 are positioned, for example, in at least one of the front nose, a side mirror, the rear bumper, the back door, or the upper part of the windshield in the vehicle compartment of a vehicle 7900. The imaging unit 7910 attached to the front nose and the imaging unit 7918 attached to the upper part of the windshield in the vehicle compartment chiefly acquire images of the area ahead of the vehicle 7900. The imaging units 7912 and 7914 attached to the side mirrors chiefly acquire images of the areas on the sides of the vehicle 7900. The imaging unit 7916 attached to the rear bumper or the back door chiefly acquires images of the area behind the vehicle 7900. The imaging unit 7918 attached to the upper part of the windshield in the vehicle compartment is used chiefly to detect a preceding vehicle, a pedestrian, an obstacle, a traffic light, a traffic sign, a lane, or the like.

Note that FIG. 24 illustrates an example of the respective imaging ranges of the imaging units 7910, 7912, 7914, and 7916. An imaging range a represents the imaging range of the imaging unit 7910 attached to the front nose. Imaging ranges b and c respectively represent the imaging ranges of the imaging units 7912 and 7914 attached to the side mirrors. An imaging range d represents the imaging range of the imaging unit 7916 attached to the rear bumper or the back door. For example, overlaying image data captured by the imaging units 7910, 7912, 7914, and 7916 offers an overhead image that looks down on the vehicle 7900.

Vehicle outside information detecting units 7920, 7922, 7924, 7926, 7928, and 7930 attached to the front, the rear, the sides, the corners, and the upper part of the windshield in the vehicle compartment of the vehicle 7900 may be, for example, ultrasonic sensors or radar apparatuses. The vehicle outside information detecting units 7920, 7926, and 7930 attached to the front nose, the rear bumper, the back door, and the upper part of the windshield in the vehicle compartment of the vehicle 7900 may be, for example, LIDAR apparatuses. These vehicle outside information detecting units 7920 to 7930 are used mainly for detecting a preceding vehicle, a pedestrian, an obstacle, or the like.

The description will continue with reference to FIG. 23 again. The vehicle outside information detecting unit 7400 causes the imaging unit 7410 to capture images of the outside of the vehicle, and receives the captured image data. In addition, the vehicle outside information detecting unit 7400 receives detection information from the connected vehicle outside information detector 7420. When the vehicle outside information detector 7420 is an ultrasonic sensor, a radar apparatus, or a LIDAR apparatus, the vehicle outside information detecting unit 7400 causes ultrasound, radio waves, or the like to be transmitted, and receives the information of the received reflected waves. The vehicle outside information detecting unit 7400 may perform processing of detecting an object such as a person, a car, an obstacle, a traffic sign, or a letter on a road, or processing of detecting the distance on the basis of the received information. The vehicle outside information detecting unit 7400 may perform environment recognition processing of recognizing a rainfall, a fog, a road condition, or the like on the basis of the received information. The vehicle outside information detecting unit 7400 may compute the distance to an object outside the vehicle on the basis of the received information.

Moreover, the vehicle outside information detecting unit 7400 may perform image recognition processing of recognizing a person, a car, an obstacle, a traffic sign, a letter on a road, or the like, or processing of detecting the distance on the basis of the received image data. The vehicle outside information detecting unit 7400 may perform distortion correcting processing, positioning processing, or the like on the received image data, and combine image data captured by a different imaging unit 7410 to generate an overhead view or a panoramic image. The vehicle outside information detecting unit 7400 may use the image data captured by the other imaging unit 7410 to perform viewpoint converting processing.

The vehicle inside information detecting unit 7500 detects information regarding the inside of the vehicle. The vehicle inside information detecting unit 7500 is connected, for example, to a driver state detector 7510 that detects the state of the driver. The driver state detector 7510 may include a camera that images the driver, a biological sensor that detects biological information of the driver, a microphone that collects sound in the vehicle compartment, or the like. The biological sensor is attached, for example, to a seating face, the steering wheel, or the like, and detects biological information of the passenger sitting on the seat or the driver gripping the steering wheel. The vehicle inside information detecting unit 7500 may compute the degree of the driver's tiredness or the degree of the driver's concentration or determine whether or not the driver have a doze, on the basis of detection information input from the driver state detector 7510. The vehicle inside information detecting unit 7500 may perform processing such as noise cancelling processing on the collected sound signal.

The integrated control unit 7600 controls the overall operation inside the vehicle control system 7000 according to various programs. The integrated control unit 7600 is connected to an input unit 7800. The input unit 7800 is implemented as an apparatus, for example, a touch panel, a button, a microphone, a switch, a lever, or the like on which a passenger can perform an input operation. The integrated control unit 7600 may receive data acquired by recognizing the voice input via the microphone. The input unit 7800 may be, for example, a remote control apparatus that uses infrared light or other radio waves, or an external connection apparatus such as a mobile telephone or a personal digital assistant (PDA) corresponding to the operation of the vehicle control system 7000. The input unit 7800 may be, for example, a camera. In that case, a passenger can input information via gesture. Alternatively, data may be input that is acquired by detecting the movement of a wearable apparatus worn by a passenger. Moreover, the input unit 7800 may include an input control circuit or the like that generates an input signal, for example, on the basis of information input by a passenger or the like using the above-described input unit 7800, and outputs the generated input signal to the integrated control unit 7600. The passenger or the like operates this input unit 7800, thereby inputting various types of data to the vehicle control system 7000 or instructing the vehicle control system 7000 about a processing operation.

The storage unit 7690 may include a read only memory (ROM) that stores various programs to be executed by a microcomputer, and a random access memory (RAM) that stores various parameters, operation results, sensor values, or the like. In addition, the storage unit 7690 may be implemented by a magnetic storage device such as a hard disk drive (HDD), a semiconductor storage device, an optical storage device, a magneto-optical storage device, or the like.

The general-purpose communication I/F 7620 is a general-purpose communication I/F that mediates in communication between various apparatuses in an external environment 7750. The general-purpose communication I/F 7620 may implement a cellular communication protocol such as global system of mobile communications (GSM (registered trademark)), WiMAX, long term evolution (LTE) or LTE-advanced (LTE-A), or other wireless communication protocols such as a wireless LAN (which is also referred to as Wi-Fi (registered trademark)) or Bluetooth (registered trademark). The general-purpose communication I/F 7620 may be connected to an apparatus (such as an application server or a control server) on an external network (such as the Internet, a cloud network, or a network specific to a service provider), for example, via a base station or an access point. In addition, the general-purpose communication I/F 7620 may be connected to a terminal (such as a terminal of the driver, a pedestrian or a store, or a machine type communication (MTC) terminal) in the vicinity of the vehicle, for example, using the peer-to-peer (P2P) technology.

The dedicated communication I/F 7630 is a communication I/F that supports a communication protocol defined for the purpose of use for vehicles. The dedicated communication I/F 7630 may implement a standard protocol, for example, wireless access in vehicle environment (WAVE), which is a combination of IEEE 802.11p for the lower layer and IEEE 1609 for the upper layer, dedicated short range communications (DSRC), or a cellular communication protocol. The dedicated communication I/F 7630 typically performs V2X communication. The V2X communication is a concept including one or more of vehicle-to-vehicle communication, vehicle-to-infrastructure communication, vehicle-to-home communication, and vehicle-to-pedestrian communication.

The positioning unit 7640 receives, for example, global navigation satellite system (GNSS) signals (such as global positioning system (GPS) signals from a GPS satellite) from a GNSS satellite for positioning, and generates position information including the latitude, longitude, and altitude of the vehicle. Here, it is to be noted that the positioning unit 7640 may also identify the present position by exchanging signals with a wireless access point, or acquire position information from a terminal such as a mobile phone, a PHS, or a smartphone that has a positioning function.

The beacon receiving unit 7650 receives radio waves or electromagnetic waves, for example, from a wireless station or the like installed on the road, and acquires information such as the present position, traffic congestion, closed roads, or necessary time. Here, it is to be noted that the function of the beacon receiving unit 7650 may be included in the above-described dedicated communication I/F 7630.

The onboard apparatus I/F 7660 is a communication interface that mediates in connections between the microcomputer 7610 and various onboard apparatuses 7760 in the vehicle. The onboard apparatus I/F 7660 may use a wireless communication protocol such as a wireless LAN, Bluetooth (registered trademark), near field communication (NFC), or a wireless USB (WUSB) to establish a wireless connection. In addition, the onboard apparatus I/F 7660 may also establish a wired connection such as a universal serial bus (USB), a high-definition multimedia interface (HDMI (registered trademark)), or a mobile high-definition link (MHL) via a connection terminal (not illustrated) (and a cable when necessary). The onboard apparatuses 7760 may include, for example, at least one of a mobile apparatus of a passenger, a wearable apparatus of a passenger, or an information apparatus carried into or attached to the vehicle. In addition, the onboard apparatuses 7760 may also include a navigation apparatus that searches for routes to any destination. The onboard apparatus I/F 7660 exchanges control signals or data signals with these onboard apparatuses 7760.

The in-vehicle network I/F 7680 is an interface that mediates in communication between the microcomputer 7610 and the communication network 7010. The in-vehicle network I/F 7680 transmits and receives signals or the like in compliance with a predetermined protocol supported by the communication network 7010.

The microcomputer 7610 of the integrated control unit 7600 controls the vehicle control system 7000 according to various programs on the basis of information acquired via at least one of the general-purpose communication I/F 7620, the dedicated communication I/F 7630, the positioning unit 7640, the beacon receiving unit 7650, the onboard apparatus I/F 7660, or the in-vehicle network I/F 7680. For example, the microcomputer 7610 may calculate a control target value of the driving force generating apparatus, the steering mechanism, or the braking apparatus on the basis of acquired information regarding the inside and outside of the vehicle, and output a control instruction to the drive system control unit 7100. For example, the microcomputer 7610 may perform cooperative control for the purpose of executing the functions of an advanced driver assistance system (ADAS) including vehicle collision avoidance or impact reduction, follow-up driving based on the inter-vehicle distance, constant vehicle speed driving, vehicle collision warning, vehicle lane departure warning, or the like. In addition, the microcomputer 7610 may control the driving force generating apparatus, the steering mechanism, the braking apparatus, or the like on the basis of acquired information regarding the areas around the vehicle, thereby performing cooperative control for the purpose of automatic driving or the like that allows the vehicle to autonomously travel irrespective of any operation of a driver.

The microcomputer 7610 may generate three-dimensional distance information regarding the distance between the vehicle and an object such as a nearby structure or person on the basis of information acquired via at least one of the general-purpose communication I/F 7620, the dedicated communication I/F 7630, the positioning unit 7640, the beacon receiving unit 7650, the onboard apparatus I/F 7660, or the in-vehicle network I/F 7680, and create local map information including surrounding information regarding the present position of the vehicle. Moreover, the microcomputer 7610 may predict danger such as vehicle collisions, approaching pedestrians or the like, or entry to closed roads on the basis of acquired information, and generate a warning signal. The warning signal may be, for example, a signal used to generate a warning sound or turn on the warning lamp.

The sound and image output unit 7670 transmits an output signal of at least one of sound or images to an output apparatus capable of visually or aurally notifying a passenger of the vehicle or the outside of the vehicle of information. In the example of FIG. 23, an audio speaker 7710, a display unit 7720, and an instrument panel 7730 are exemplified as the output apparatus. For example, the display unit 7720 may include at least one of an onboard display or a head-up display. The display unit 7720 may have an augmented reality (AR) display function. The output apparatus may also be an apparatus other than these apparatuses like a headphone, a wearable apparatus such as a glasses-type display worn by a passenger, a projector, a lamp, or the like. In a case in which the output apparatus is a display, the display visually displays a result acquired by the microcomputer 7610 performing various processings or information received from another control unit in various forms such as text, images, tables, or graphs. In addition, in a case in which the output apparatus is a sound output apparatus, the sound output apparatus converts sound signals including reproduced sound data, acoustic data, or the like into analog signals, and aurally outputs the analog signals.

Note that, in the example illustrated in FIG. 23, at least two control units connected via the communication network 7010 may be integrated into one control unit. Alternatively, the respective control units may be configured as a plurality of control units. Moreover, the vehicle control system 7000 may also include another control unit that is not illustrated. Moreover, a part or the whole of the functions executed by any of the control units may be executed by another control unit in the above description. That is, as long as information is transmitted and received via the communication network 7010, predetermined operation processing may be performed by any of the control units. Similarly, a sensor or an apparatus connected to any of the control units may be connected to another control unit, and the control units may transmit and receive detection information to and from each other via the communication network 7010.

Here, a computer program for realizing the functions of the imaging apparatus 100 (or the imaging apparatus 100a and the imaging apparatus 100b according to the second embodiment) according to the first embodiment described above may be implemented on any one of control units and the like. Moreover, a computer-readable recording medium having the computer program stored therein may be provided. The recording medium is a magnetic disk, an optical disc, an opto-magnetic disc, a flash memory, or the like, for example. Moreover, the computer program may be distributed via a network, for example, without using a recording medium.

Moreover, in the vehicle control system 7000, the imaging apparatus 100 (or the imaging apparatus 100a and the imaging apparatus 100b according to the second embodiment) according to the first embodiment described above can be realized by the imaging unit 7410 (or the vehicle state detector 7110, the vehicle outside information detector 7420, the driver state detector 7510, and the like).

Moreover, at least some components of the imaging apparatus 100 (or the imaging apparatus 100a and the imaging apparatus 100b according to the second embodiment) according to the first embodiment described above may be realized by a module (for example, an integrated circuit module formed as a single die) for the integrated control unit 7600 illustrated in FIG. 23. Alternatively, the imaging apparatus 100 (or the imaging apparatus 100a and the imaging apparatus 100b according to the second embodiment) according to the first embodiment described above may be realized by a plurality of control units of the vehicle control system 7000 illustrated in FIG. 23.

Hereinabove, the preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Moreover, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present disclosure may also be configured as below.

(1)

An imaging apparatus including:

a splitter that splits incident light into pieces of light of two or more wavelength bands; and two or more detectors that detect the pieces of light of two or more wavelength bands and output signals from which wavelengths can be extracted tunably by post-processing.

(2)

The imaging apparatus according to (1), in which the two or more detectors each include filter having a different spectral characteristic in units of pixels.

(3)

The imaging apparatus according to (2), in which the two or more detectors have approximately the same spectral characteristics.

(4)

The imaging apparatus according to (2), in which the two or more detectors have different spectral characteristics.

(5)

The imaging apparatus according to (4), in which the spectral characteristic of each the two or more detectors is determined depending on the wavelength band of detection target light.

(6)

The imaging apparatus according to any one of (1) to (5), in which the splitter splits the incident light into light of a visible wavelength or smaller and light of wavelengths longer than the visible wavelength.

(7)

The imaging apparatus according to any one of (1) to (6), in which the splitter includes a splitting surface in which the incident light is split into pieces of light of two or more wavelength bands, and the splitting surface is disposed so as to have a predetermined angle with respect to an optical axis of the incident light.

(8)

The imaging apparatus according to (7), in which the splitter is a dichroic filter, and the dichroic filter splits the incident light into light reflected from the splitting surface and light passing through the splitting surface.

(9)

The imaging apparatus according to any one of (1) to (8), in which the incident light is emission light emitted from a light source or reflection light of the emission light reflected from a subject.

(10)

A signal processing apparatus including:

an acquiring unit that acquires signals output by two or more detectors respectively having detected pieces of light of two or more wavelength bands split from incident light by a splitter; and a signal processing unit that extracts signals of a desired wavelength band using the signals.

(11)

The signal processing apparatus according to (10), in which when the incident light is reflection light of emission light emitted from a light source and reflected from a subject, the signal processing unit outputs a value related to spectral characteristics of the reflection light using the signals.

(12)

The signal processing apparatus according to (11), in which when the incident light is the emission light, the signal processing unit outputs a value related to spectral characteristics of the emission light using the signals and outputs a value related to the spectral characteristics of the reflection light using the value related to the spectral characteristics of the emission light.

(13)

The signal processing apparatus according to (11) or (12), in which the subject is plant, and the signal processing unit calculates a vegetation index using the values related to the spectral characteristics of the reflection light.

(14)

A signal processing method to be executed by a computer, the method including:

acquiring signals output by two or more detectors respectively having detected pieces of light of two or more wavelength bands split from incident light by a splitter; and extracting signals of a desired wavelength band using the signals.

(15)

A program for causing a computer to execute:

acquiring signals output by two or more detectors respectively having detected pieces of light of two or more wavelength bands split from incident light by a splitter; and extracting signals of a desired wavelength band using the signals.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

100 Imaging apparatus
110 Imaging processing unit
111 Imaging optical system
112 Exposure processing unit
113 Tunable filter
114 Image sensor
120 Signal processing unit
130 Storage unit
140 Control unit
150 Communication unit
200 Spectroscope
300a Information processing apparatus
300b Cloud server

The invention claimed is:

1. An imaging apparatus comprising:
a splitter that splits incident light into pieces of light of two or more wavelength bands, the wavelength bands including a first wavelength band of light of a visible wavelength and a second wavelength band of only light of wavelengths longer than the visible wavelength; and
two or more detectors that respectively detect the pieces of light of two or more wavelength bands, the two or more detectors including a first detector for the first wavelength band and a second detector for the second wavelength band, and that output signals from which wavelength bands can be extracted tunably by post-processing.

2. The imaging apparatus according to claim 1, wherein the two or more detectors each include filter a having different spectral characteristic in units of pixels.

3. The imaging apparatus according to claim 2, wherein the two or more detectors have approximately the same spectral characteristics.

4. The imaging apparatus according to claim 2, wherein the two or more detectors have different spectral characteristics.

5. The imaging apparatus according to claim 4, wherein the spectral characteristic of each of the two or more detectors is determined depending on the wavelength band of detection target light.

6. The imaging apparatus according to claim 1, wherein the first wavelength band includes at least one of red, green or blue light, and the second wavelength band includes near infrared light.

7. The imaging apparatus according to claim 1, wherein the splitter includes a splitting surface in which the incident light is split into pieces of light of two or more wavelength bands, and
the splitting surface is disposed so as to have a predetermined angle with respect to an optical axis of the incident light.

8. The imaging apparatus according to claim 7, wherein the splitter is a dichroic filter, and
the dichroic filter splits the incident light into light reflected from the splitting surface and light passing through the splitting surface.

9. The imaging apparatus according to claim 1, wherein the incident light is emission light emitted from a light source or reflection light of the emission light reflected from a subject.

10. A signal processing apparatus comprising:
acquisition circuitry configured to acquire signals output by two or more detectors respectively having detected pieces of light of two or more wavelength bands split from incident light by a splitter, the wavelength bands including a first wavelength band of light of a visible wavelength and a second wavelength band of only light of wavelengths longer than the visible wavelength, the two or more detectors including a first detector for the first wavelength band and a second detector for the second wavelength band; and
a signal processor configured to extract signals of a desired wavelength band using the signals.

11. The signal processing apparatus according to claim 10, wherein
when the incident light is reflection light of emission light emitted from a light source and reflected from a subject,
the signal processor a value related to spectral characteristics of the reflection light using the signals.

12. The signal processing apparatus according to claim 11, wherein
when the incident light is the emission light,
the signal processor outputs a value related to spectral characteristics of the emission light using the signals and outputs a value related to the spectral characteristics of the reflection light using the value related to the spectral characteristics of the emission light.

13. Signal processing apparatus according to claim 11, wherein
the subject is plant, and
the signal processor calculates a vegetation index using the values related to the spectral characteristics of the reflection light.

14. A signal processing method to be executed by a computer, the method comprising:
acquiring signals output by two or more detectors respectively having detected pieces of light of two or more wavelength bands split from incident light by a splitter, the wavelength bands including a first wavelength band of light of a visible wavelength and a second wavelength band of only light of wavelengths longer than the visible wavelength, the two or more detectors including a first detector for the first wavelength band and a second detector for the second wavelength band; and
extracting signals of a desired wavelength band using the signals.

15. A non-transitory computer readable medium storing a program, the program being executable by a computer to perform operations comprising:
acquiring signals output by two or more detectors respectively having detected pieces of light of two or more wavelength bands split from incident light by a splitter, the wavelength bands including a first wavelength band of light of a visible wavelength and a second wavelength band of only light of wavelengths longer than the visible wavelength, the two or more detectors including a first detector for the first wavelength band and a second detector for the second wavelength band; and
extracting signals of a desired wavelength band using the signals.

16. The apparatus according to claim 10, wherein the first wavelength band includes at least one of red, green or blue light, and the second wavelength band includes near infrared light.

17. The method according to claim 14, wherein the first wavelength band includes at least one of red, green or blue light, and the second wavelength band includes near infrared light.

18. The non-transitory computer readable medium according to claim 15, wherein the first wavelength band includes at least one of red, green or blue light, and the second wavelength band includes near infrared light.

* * * * *